United States Patent
Irie

(10) Patent No.: US 10,098,365 B2
(45) Date of Patent: Oct. 16, 2018

(54) FRESHNESS RETAINING AGENT, METHOD FOR MANUFACTURING THE SAME, GAS PURIFICATION DEVICE, AND GAS PURIFICATION SYSTEM

(71) Applicant: TANKA CO., LTD., Saga (JP)

(72) Inventor: Yasuo Irie, Saga (JP)

(73) Assignee: TANKA CO., LTD., Saga (JP)

( * ) Notice: Subject to any disclaimer, the term of this patent is extended or adjusted under 35 U.S.C. 154(b) by 184 days.

(21) Appl. No.: 15/116,454

(22) PCT Filed: Dec. 10, 2014

(86) PCT No.: PCT/JP2014/082742
§ 371 (c)(1),
(2) Date: Aug. 12, 2016

(87) PCT Pub. No.: WO2015/114959
PCT Pub. Date: Aug. 6, 2015

(65) Prior Publication Data
US 2017/0006887 A1    Jan. 12, 2017

(30) Foreign Application Priority Data
Feb. 3, 2014 (JP) .................................. 2014-018610

(51) Int. Cl.
*A01N 25/12* (2006.01)
*A01N 25/26* (2006.01)
(Continued)

(52) U.S. Cl.
CPC ................ *A23B 7/144* (2013.01); *A01G 5/06* (2013.01); *A01N 3/00* (2013.01); *A01N 3/02* (2013.01);
(Continued)

(58) Field of Classification Search
CPC .......... A01N 25/12; A01N 25/26; A01N 3/00; A01N 59/00; A23B 7/144; A01G 5/06
See application file for complete search history.

(56) References Cited

U.S. PATENT DOCUMENTS

| | | |
|---|---|---|
| 5,536,155 A | 7/1996 | Futaki et al. |
| 2006/0150818 A1 | 7/2006 | Okamoto et al. |
| 2010/0210866 A1* | 8/2010 | Toyohara .................. A23L 2/52 560/61 |

FOREIGN PATENT DOCUMENTS

| | | |
|---|---|---|
| JP | H07-033602 A | 2/1995 |
| JP | H07-124469 A | 5/1995 |

(Continued)

OTHER PUBLICATIONS

Web site "Heisei 25 nendo Shokibo Jigyosha Kasseika Hojokin Saitaku Ichiran (Kyushu-kyoku)", <http://www.chusho.meti.go.jp/keiei/shokibo/2013/130919kyuusyu.pdf>, "No. 126 development project concerning antibacterial agent against water fungus or microorganism using bamboo charcoals, catechins and etc.", Sep. 26, 2013, 1 sheet, The Small and Medium Enterprise Agency, Tokyo, Japan.

(Continued)

*Primary Examiner* — Sean E Conley
(74) *Attorney, Agent, or Firm* — Heedong Chae; Lucem, PC

(57) ABSTRACT

Provided are a freshness retaining agent that can be obtained by a simple method and exhibits excellent adsorption performance and antibacterial activity, a gas purification device including the freshness retaining agent, and a gas purification system. The freshness retaining agent is formed by adhering tea catechins to a surface and/or an inside of charcoal powders and adhering the charcoal powders to each (Continued)

other with clay interposed between the charcoal powders, thereby exhibiting excellent adsorption performance and antibacterial activity.

6 Claims, 10 Drawing Sheets

(51) Int. Cl.
| | |
|---|---|
| A01N 3/00 | (2006.01) |
| A23B 7/144 | (2006.01) |
| A01N 43/16 | (2006.01) |
| A01G 5/06 | (2006.01) |
| A01N 3/02 | (2006.01) |
| A01N 59/00 | (2006.01) |
| A01N 59/06 | (2006.01) |
| A01N 59/16 | (2006.01) |
| A01N 65/08 | (2009.01) |
| A61L 9/18 | (2006.01) |
| B01D 53/00 | (2006.01) |
| B01D 53/04 | (2006.01) |
| B01J 20/12 | (2006.01) |
| B01J 20/20 | (2006.01) |
| B01J 20/22 | (2006.01) |
| B01J 20/30 | (2006.01) |
| A61L 2/10 | (2006.01) |
| A61L 9/20 | (2006.01) |
| B01D 53/02 | (2006.01) |
| B01D 53/14 | (2006.01) |

(52) U.S. Cl.
CPC .............. *A01N 25/12* (2013.01); *A01N 25/26* (2013.01); *A01N 43/16* (2013.01); *A01N 59/00* (2013.01); *A01N 59/06* (2013.01); *A01N 59/16* (2013.01); *A01N 65/08* (2013.01); *A61L 2/10* (2013.01); *A61L 9/18* (2013.01); *A61L 9/205* (2013.01); *B01D 53/007* (2013.01); *B01D 53/02* (2013.01); *B01D 53/04* (2013.01); *B01D 53/1418* (2013.01); *B01D 53/1493* (2013.01); *B01J 20/12* (2013.01); *B01J 20/20* (2013.01); *B01J 20/22* (2013.01); *B01J 20/3042* (2013.01); *A23V 2002/00* (2013.01); *A61L 2209/12* (2013.01); *A61L 2209/134* (2013.01); *A61L 2209/20* (2013.01); *A61L 2209/22* (2013.01); *B01D 2253/102* (2013.01); *B01D 2253/106* (2013.01); *B01D 2253/11* (2013.01); *B01D 2253/1122* (2013.01); *B01D 2253/20* (2013.01); *B01D 2253/25* (2013.01); *B01D 2255/20707* (2013.01); *B01D 2255/802* (2013.01); *B01D 2257/80* (2013.01); *B01D 2257/91* (2013.01); *B01D 2258/0275* (2013.01); *B01D 2258/06* (2013.01); *B01D 2259/802* (2013.01)

(56) References Cited

FOREIGN PATENT DOCUMENTS

| | | |
|---|---|---|
| JP | H07-289888 A | 11/1995 |
| JP | H08-291013 A | 11/1996 |
| JP | H10-001401 A | 1/1998 |
| JP | H11-302547 A | 11/1999 |
| JP | H11-332535 A | 12/1999 |
| JP | 2001-070419 A | 3/2001 |
| JP | 2001-157706 A | 6/2001 |
| JP | 2002-159224 A | 6/2002 |
| JP | 2003-047648 A | 2/2003 |
| JP | 2005-160494 A | 6/2005 |
| JP | 2005-198854 A | 7/2005 |
| JP | 2006-129707 A | 5/2006 |
| JP | 2006-159086 A | 6/2006 |
| JP | 2006-218386 A | 8/2006 |
| JP | 2006-224994 A | 8/2006 |
| JP | 2011-212098 A | 10/2011 |

OTHER PUBLICATIONS

International Search Report issued in Application No. PCT/JP2014/082742, dated Mar. 10, 2015.

* cited by examiner

FIG.6
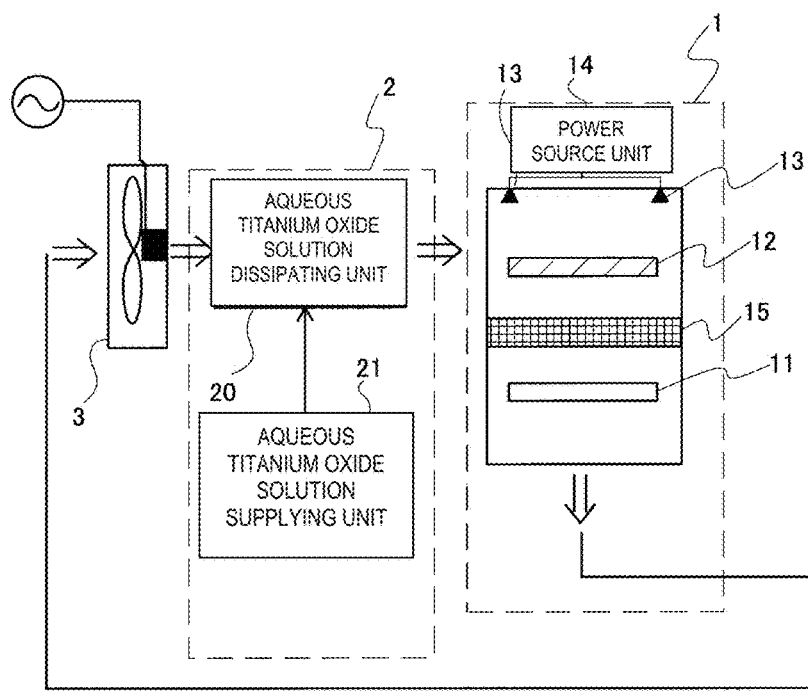
(a)
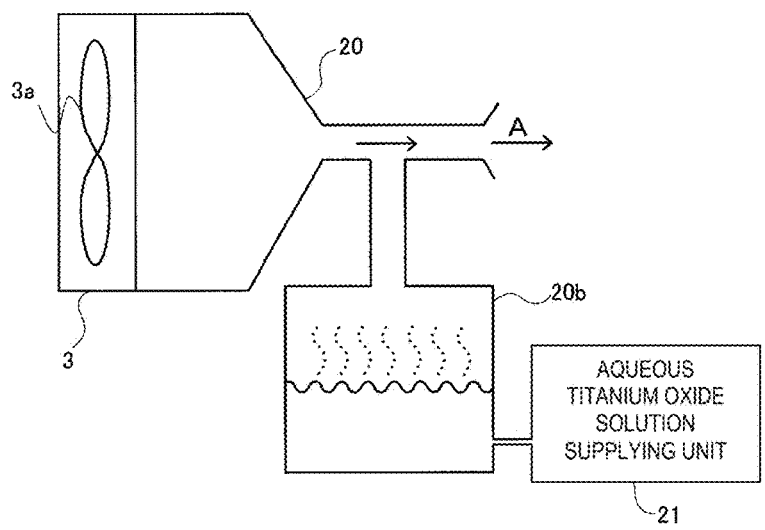
(b)

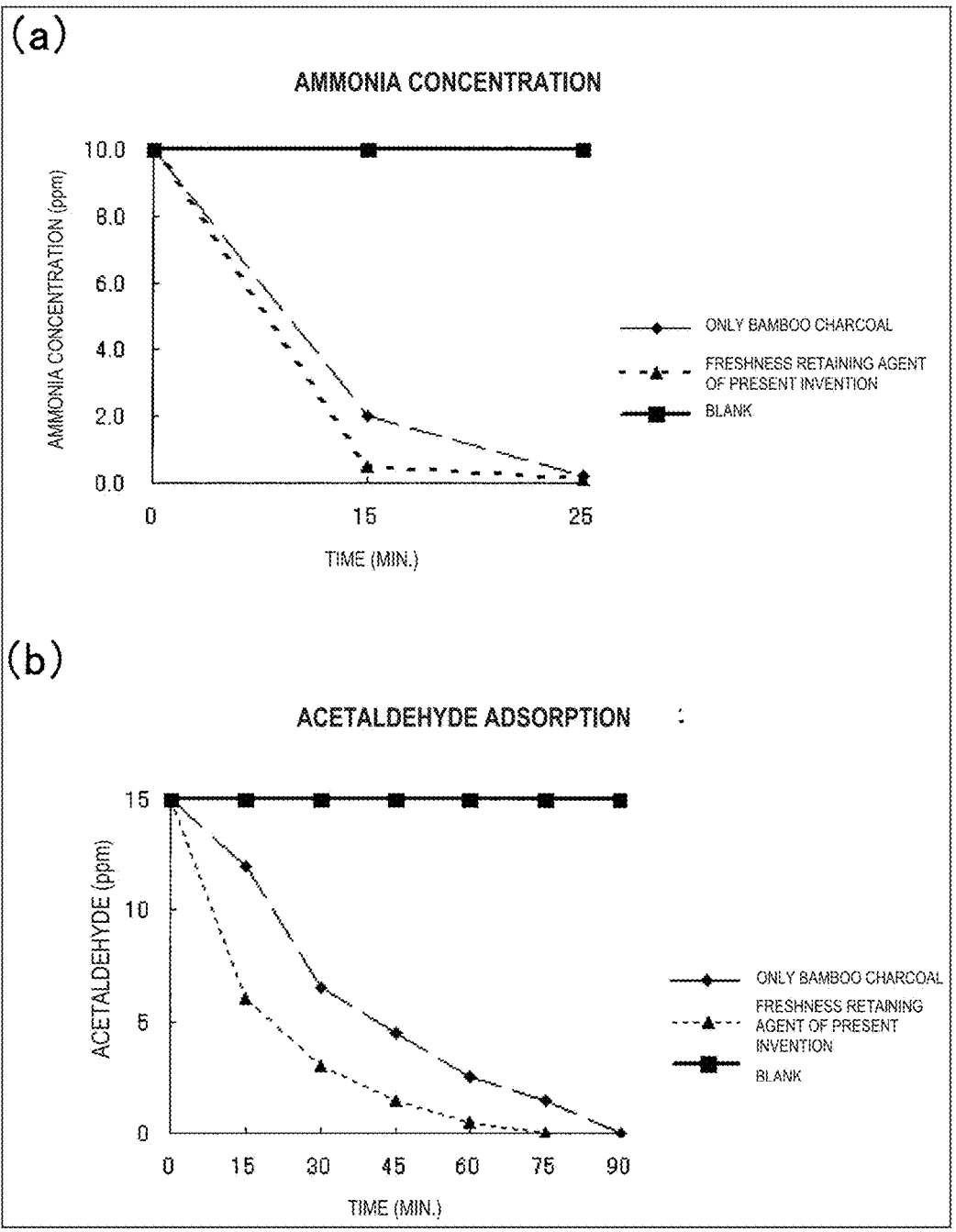

FRESHNESS RETAINING AGENT, METHOD FOR MANUFACTURING THE SAME, GAS PURIFICATION DEVICE, AND GAS PURIFICATION SYSTEM

TECHNICAL FIELD

The present invention relates to a freshness retaining agent that mainly retains freshness of fruit and vegetables or flowers, a method for manufacturing the same, a gas purification device, and a gas purification system, and particularly relates to a freshness retaining agent using bamboo charcoal, a method for manufacturing the same, a gas purification device, and a gas purification system.

BACKGROUND ART

As a commercial value of fruit and vegetables and flowers, freshness is the most important factor. However, the fruit and vegetables and the flowers are perishable due to decomposition gas such as ethylene gas, ammonia gas, or acetaldehyde that is released from themselves and induces decomposition. For this reason, there is a problem that after-ripening, softening, or tarnishing progresses with the lapse of time, whereby freshness declines and a commercial value sharply decreases.

For example, with respect to a cut flower out of flowers, withering of floral leaves or falling of buds easily occurs due to generation of ethylene gas. In addition, by decay of vase water or stems or clogging of stems with chemical substances or bacteria, water absorption is suppressed and withering of leaves or flowers is likely to occur.

In order to suppress such deterioration of freshness, for example, a method for facilitating water absorption using a surfactant (ion-based), a method for acidifying vase water with a sulfate, a nitrate, or an aluminum sulfate and using the acidified water as an antibacterial agent or a bacteriostatic agent, and a method for suppressing generation of ethylene gas using a silver thiosulfate have been known from the related art. In these methods, however, it is difficult for general users to handle chemicals to be used, because concentration management of the chemicals is hard, heavy metals are contained in the chemicals, or the chemicals are very expensive.

Under such circumstances, a freshness retaining agent (gas purification agent) is desired which is handled with ease and has gas purification action to suppress an adverse effect to be caused by decomposition gas, thereby being capable of retaining freshness of fruit and vegetables or flowers over a long period of time. As such a freshness retaining agent, there has been proposed a freshness retaining agent using a carbon-based material such as bamboo charcoal or wood charcoal which is a familiar material originated from a natural product and has excellent adsorption performance of gas.

For example, as a freshness retaining agent of the related art, there is a freshness retaining paper for vegetables and the like (see PTL 1) which is formed by coating a mixture obtained by kneading a styrene-acrylic copolymer binder with charcoal powders on a stored article facing side of an easily disintegrable/moisture-proof/waterproof paper and has easily disintegrable/moisture-proof/waterproof and decomposition gas adsorption performance, wherein the styrene-acrylic copolymer binder is obtained by a hydrosol method and adjustment of a glass transition temperature in a range of 65 to 75° C., and the easily disintegrable/moisture-proof/waterproof paper is formed by being dried at a temperature of the minimum film forming temperature (MFT) or higher.

In addition, a wet-type gel deodorant has also been proposed. For example, there is a gel deodorant in which a carbon-based adsorbent such as activated charcoal, wood charcoal, or bamboo charcoal or a silica-based adsorbent is dispersed into a gel (see PTL 2). Further, there is also a gel antibacterial deodorant in which an adsorbent selected from powder of activated charcoal, Bincho-charcoal, bamboo charcoal, or wood charcoal and a plant antibacterial component are dispersed into a gel (see PTL 3).

CITATION LIST

Patent Literature

[PTL 1] Japanese Unexamined Patent Application Publication No. 2006-224994
[PTL 2] Japanese Unexamined Patent Application Publication No. 2001-157706
[PTL 3] Japanese Unexamined Patent Application Publication No. 2003-47648

SUMMARY OF INVENTION

Technical Problem

However, the freshness retaining agent according to the related art has practical problems as follows. In order to obtain the freshness retaining paper disclosed in PTL 1, first, a working process is required to prepare the styrene-acrylic copolymer binder so as to be suitable for use as a raw material. In addition, a control process is also required to perform the drying at the temperature equal to or higher than the minimum film-forming temperature (MFT). Thus, since complicated processes are required, the freshness retaining paper is not easily obtained. Furthermore, when various bacteria once propagate during use for retention of the freshness, since no treatment against these bacteria is performed, unsanitary condition is continuously maintained, and thus there is a fundamental problem that the freshness cannot be retained.

In addition, with respect to the wet-type gel deodorant as disclosed in PTL 2 or PTL 3, it is intended to primarily facilitate adsorption of water soluble gas using a wet state of the gel, but there is a problem that hardly soluble gas (for example, ethylene gas) against water is hardly adsorbed using the wet state of the gel.

In addition, with respect to the freshness retaining agent (gas cleaning agent) of the related art, since a range in which adsorption performance can be exerted is narrow, there is also a problem of being limited to use of a relatively narrow space during actual gas cleaning. From this viewpoint, although needs for gas cleaning in a closed space for a long time with a relatively large volume (for example, refrigerators, crop storehouses, sheaves (containers), and in-warehouse) is strong, there are no gas purification device and gas purification system that meet the needs at the present time.

The present invention has been made to solve the problems, and an object thereof is to provide a freshness retaining agent that purifies gas subjected to gas purification (target gas) regardless of water solubility thereof, also has antibacterial activity, and can be more easily manufactured, a method for manufacturing the same, a gas purification device including the freshness retaining agent, and a gas purification system.

Solution to Problem

A freshness retaining agent disclosed in the present application is formed by adhering tea catechins to a surface and/or an inside of charcoal powders and adhering the charcoal powders to each other with clay interposed between the charcoal powders. Thus, since the freshness retaining agent disclosed in the present application is formed by making the tea catechin and the clay adhere to the surface of the charcoal powder, adsorptive capacity of the charcoal powder and antibacterial capability due to the tea catechin are combined with each other through the clay to exhibit a synergistic effect, antifungal effect and humidity conditioning effect can be also exerted in addition to excellent gas adsorption performance and antibacterial activity.

In the freshness retaining agent disclosed in the present application, as necessary, the charcoal powder is one or more selected from bamboo charcoal, wood charcoal, or activated charcoal. Thus, in the freshness retaining agent disclosed in the present application, since the charcoal powder is a material having excellent adsorptive capacity and being easily available, manufacturing costs are suppressed, desired gas adsorption performance is obtained, and higher gas adsorption performance and antibacterial activity can be exerted at a low cost.

In the freshness retaining agent disclosed in the present application, as necessary, the clay is one or more selected from bentonite, montmorillonite, hectorite, laponite, silica, starch, gelatin, guar gum, gum arabic, methyl cellulose, or ethyl cellulose. Thus, in the freshness retaining agent disclosed in the present application, since the clay is a material having high viscosity and being easily available, manufacturing costs are suppressed, the charcoal powder and the tea catechin are firmly fixed by the viscosity, and higher gas adsorption performance and antibacterial activity can be exerted at a low cost.

In the freshness retaining agent disclosed in the present application, as necessary, a silver compound adheres to the surface and/or the inside of the charcoal powder. Thus, since the silver compound adheres to the surface and/or the inside of the charcoal powder, the silver compound acts on the gas (target gas), whereby adsorption performance of gas adsorption and antibacterial activity against bacteria can be simultaneously enhanced, and high freshness retaining performance is obtained.

In addition, a gas purification device using the freshness retaining agent disclosed in the present application includes a gas treatment unit that adsorbs gas components contained in a target gas using the freshness retaining agent. Thus, since the gas treatment unit is provided to adsorb the gas components contained in the target gas using the freshness retaining agent, the gas components contained in the target gas are adsorbed by the freshness retaining agent and are subjected to antibacterial action at the same time, and antifungal effect and humidity conditioning effect can be exerted and purification can be performed with respect to the target gas.

In the gas purification device disclosed in the present application, as necessary, the gas purification device further includes: a titanium oxide treatment unit that has a coated surface coated with a titanium oxide; and a light source unit that irradiates the titanium oxide treatment unit with light. Thus, since the titanium oxide treatment unit coated with the titanium oxide and the light source unit that irradiates the titanium treatment unit with light, the titanium oxide component contained in the droplets acts as a photocatalyst with light irradiation by the light source unit to directly and additionally exhibit the sterilizing effect with respect to the target gas, sterilizing, bacterial killing, eradication of bacteria, and an adsorption treatment are performed in a multiple manner in the inside of the gas purification device 1, and a gas-cleaned state can be efficiently maintained for a long time.

In the gas purification device disclosed in the present application, as necessary, the light source unit is disposed oppositely to the coated surface of the titanium oxide treatment unit, and the titanium oxide treatment unit is disposed above or below the gas treatment unit. Thus, since the light source unit is disposed oppositely to the coated surface of the titanium oxide treatment unit and the titanium oxide treatment unit is disposed above or below the gas treatment unit, the photocatalytic action is exerted on the coated surface of the titanium oxide treatment unit, sterilizing, eradication of bacteria, and degradation treatment can be efficiently performed with respect to the target gas passing through the titanium oxide treatment unit.

In the gas purification device disclosed in the present application, as necessary, the gas purification device further includes a light shielding unit that is disposed between the gas treatment unit and the light source unit to shield light. Thus, since the light shielding unit disposed between the gas treatment unit and the light source unit is provided to shield light, unnecessary light irradiation from the light source unit is blocked with respect to the gas treatment unit, deterioration of the gas treatment unit due to the light irradiation is prevented, and gas purification performance can be further maintained over a long period of time.

In addition, a gas purification system including the gas purification device disclosed in the present application includes an aqueous titanium oxide solution supplying unit that supplies an aqueous titanium oxide solution, and an aqueous titanium oxide solution dissipating unit that dissipates droplets of the aqueous titanium oxide solution supplied by the aqueous titanium oxide solution supplying unit, wherein the target gas passes through the aqueous titanium oxide solution dissipating unit and is supplied to the gas purification device. Thus, the aqueous titanium oxide solution supplying unit that supplies the aqueous titanium oxide solution and the aqueous titanium oxide solution dissipating unit that dissipates droplets of the aqueous titanium oxide solution supplied by the aqueous titanium oxide solution supplying unit are provided, the target gas passes through the aqueous titanium oxide solution dissipating unit and is supplied to the gas purification device, and thus the target gas mixed with the droplets containing the titanium oxide is supplied to the gas purification device, whereby antibacterial action, sterilizing, and eradication of bacteria are exerted by the titanium oxide with respect to the high-humidity target gas into which the droplets of the aqueous titanium oxide solution are dissipated, adsorption due to the freshness retaining agent provided in the gas purification device is performed in a multiple manner, and the freshness can be further maintained for a long time.

In particular, when the light source unit is disposed in the gas purification device, the titanium oxide contained in the target gas is optically activated by the light irradiation from the light source unit, the target gas passes through the freshness retaining agent after passing through the titanium oxide treatment unit in which the target gas is optically activated, degradation due to the titanium oxide, adsorption, antibacterial action, sterilizing, and eradication of bacteria due to the freshness retaining agent are exerted with respect to the target gas in a multiple manner, and freshness can be further maintained for a long time.

In the gas purification system disclosed in the present application, as necessary, the aqueous titanium oxide solution dissipating unit generates and dissipates droplets having a size containing at least an aqueous titanium oxide solution component by ultrasonic vibration. Thus, the aqueous titanium oxide solution dissipating unit generates and dissipates droplets having the size containing at least the aqueous titanium oxide solution component by the ultrasonic vibration, whereby the droplets having the size containing at least the aqueous titanium oxide solution component but not being obtained by simple vaporization are easily and reliably generated by fine ultrasonic vibration, and antibacterial action, sterilizing, degradation, and eradication of bacteria due to the titanium oxide can be reliably exerted with respect to the target gas.

In the gas purification system disclosed in the present application, as necessary, the aqueous titanium oxide solution dissipating unit generates and dissipates droplets having a size containing at least an aqueous titanium oxide solution component by flash evaporation using a decompression chamber. Thus, since the aqueous titanium oxide solution dissipating unit generates and dissipates the droplets having the size containing at least the aqueous titanium oxide solution component by the flash evaporation using the decompression chamber, power according to the aqueous titanium oxide solution dissipating unit is not necessary, antibacterial action, sterilizing, degradation, and eradication of bacteria due to the titanium oxide are easily and reliably exerted with respect to the target gas even under a condition where the supply of power is difficult, and gas cleaning can be performed.

In the gas purification system disclosed in the present application, as necessary, the aqueous titanium oxide solution dissipating unit generates and dissipates droplets having a size containing at least an aqueous titanium oxide solution component by a net body immersed in the aqueous titanium oxide solution of the aqueous titanium oxide solution supplying unit. Thus, since the aqueous titanium oxide solution dissipating unit generates and dissipates the droplets having the size containing at least the aqueous titanium oxide solution component by the net body immersed in the aqueous titanium oxide solution of the aqueous titanium oxide solution supplying unit, the aqueous titanium oxide solution can be sucked up onto the net body by capillary action, the titanium oxide solution is contained in the target gas when the target gas passes through the net body, antibacterial action, sterilizing, degradation, and eradication of bacteria due to the titanium oxide are easily and reliably exerted with respect to the target gas with a simpler configuration even under a condition where the supply of power is difficult, and gas cleaning can be performed.

In the gas purification system disclosed in the present application, as necessary, the system further includes a power acquisition unit that extracts power from a magnetic field generated in a current generated from the outside, and the power extracted by the power acquisition portion is supplied to the light source unit and/or the aqueous titanium oxide solution dissipating unit. Thus, since the power acquisition unit is provided to extract the power from the magnetic field generated in the current generated from the outside and the power extracted by the power acquisition unit is supplied to the light source unit and/or the aqueous titanium oxide solution dissipating unit, the power is supplied using an external power source, and a gas purification treatment stably continues even in a situation where the power source cannot be utilized in the gas purification system.

A method for manufacturing a freshness retaining agent disclosed in the present application includes: a mixing step of mixing tea catechins, charcoal powders, and clay with each other to obtain a mixed solution; a gelling step of obtaining a gel-like body using a gelling agent with respect to the mixed solution obtained by the mixing step; and a drying step of drying the gel-like body obtained by the gelling step. Thus, in the method for manufacturing the freshness retaining agent disclosed in the present application, the mixed solution is obtained in the mixing step by mixing the tea catechin, the charcoal powder, and the clay with each other, the gel-like body is obtained in the gelling step using the gelling agent with respect to the mixed solution obtained by the mixing step, and the gel-like body is dried in the drying step, whereby the gel-like body is dried, thereby obtaining a high specific surface area, and it is possible to obtain the freshness retaining agent having high gas adsorption performance and antibacterial activity.

In the method for manufacturing the freshness retaining agent disclosed in the present application, as necessary, the mixed solution is obtained in the mixing step by mixing the tea catechins, the charcoal powders, and the clay with an aqueous binder solution consisting of a water-soluble polymer, and the gel-like body is obtained in the gelling step by dropping the mixed solution obtained by the mixing step into a potassium or calcium-containing aqueous solution. Thus, in the method for manufacturing the freshness retaining agent disclosed in the present application, the mixed solution is obtained in the mixing step by mixing the tea catechin, the charcoal powder, and the clay with the aqueous binder solution consisting of the water-soluble polymer, the gel-like body is obtained in the gelling step by dropping of the mixed solution into the potassium or calcium-containing aqueous solution, and the gel-like body is dried in the drying step, whereby the gel-like body is formed by a simple operation such as dropping, and it is possible to obtain the freshness retaining agent having high gas adsorption performance and antibacterial activity at a lower cost.

In the method for manufacturing the freshness retaining agent disclosed in the present application, as necessary, the charcoal powder is one or more selected from bamboo charcoal, wood charcoal, or activated charcoal. Thus, in the method for manufacturing the freshness retaining agent disclosed in the present application, since the charcoal powder is a material having excellent adsorptive capacity and being easily available, manufacturing costs are suppressed, desired gas adsorption performance is obtained, and it is possible to obtain the freshness retaining agent having high gas adsorption performance and antibacterial activity at a low cost.

In the method for manufacturing the freshness retaining agent disclosed in the present application, as necessary, the clay is one or more selected from bentonite, montmorillonite, hectorite, laponite, silica, starch, gelatin, guar gum, gum arabic, methyl cellulose, or ethyl cellulose. Thus, in the method for manufacturing the freshness retaining agent disclosed in the present application, since the clay is a material having high viscosity and being easily available, manufacturing costs are suppressed, the charcoal powder and the tea catechin are firmly fixed by the viscosity, and it is possible to obtain the freshness retaining agent having high gas adsorption performance and antibacterial activity at a low cost.

In the method for manufacturing the freshness retaining agent disclosed in the present application, as necessary, the water-soluble polymer is any one of sodium alginate, potassium alginate, or ammonium alginate, and the potassium or calcium-containing aqueous solution is either one of potassium chloride or calcium chloride. Thus, in the method for manufacturing the freshness retaining agent disclosed in the present application, since the alginate is used, a raw material being easily available and being suitable for gelling is used in the gelling step, and it is possible to easily obtain the freshness retaining agent having gas adsorption performance and antibacterial activity at a low cost.

In the method for manufacturing the freshness retaining agent disclosed in the present application, the drying in the drying step is performed by firing at 80° C. to 100° C. Thus, in the freshness retaining agent disclosed in the present application, since the drying in the drying step is performed by the firing at 80° C. to 100° C., the drying is facilitated in the gel state without degradation of the tea catechin, the tea catechin effectively adheres to the charcoal powder, and it is possible to obtain the freshness retaining agent having high gas adsorption performance and antibacterial activity.

BRIEF DESCRIPTION OF THE DRAWINGS

FIG. 6 illustrates a block diagram of a gas purification system according to a tenth embodiment of the present invention and an explanatory diagram of a structure of a titanium oxide dissipating unit.

FIG. 10 illustrates adsorption test results of the freshness retaining agent according to the embodiment of the present invention.

BEST MODE FOR CARRYING OUT THE INVENTION

First Embodiment

A freshness retaining agent according to a first embodiment will be described below. The freshness retaining agent according to the first embodiment is formed by adhering tea catechins to the surface and/or the inside of charcoal powders and adhering the charcoal powders to each other with clay interposed between the charcoal powders.

The tea catechin is not particularly limited as long as being a catechin extracted from tea leaves, and may make use of a tea catechin extracted from a commercially available Japanese tea, for example. In addition, the tea catechin can make use of third-picked tea or tea-leave pruned branches called waste materials (tea residual materials) in addition to commercialized products, and, in this case, it is possible to achieve effective utilization of resources and suppression of manufacturing costs.

For example, the charcoal powder can be selected from one or more of bamboo charcoal, wood charcoal, or activated charcoal, but the bamboo charcoal is preferably used in terms of ease of handling and availability. A commercialized product can be also used as the bamboo charcoal without being changed. However, the bamboo charcoal can be also obtained by firing (for example, 600° C. to 800° C.) of commercially available bamboo or bamboo in a neglected bamboo forest, and, in this case, it is possible to achieve effective utilization of resources and suppression of manufacturing costs. The size of the charcoal powder is not particularly limited, but, for example, a charcoal powder of micrometer order can be used.

The clay can be selected from one or more of bentonite, montmorillonite, hectorite, laponite, silica, starch, gelatin, guar gum, gum arabic, methyl cellulose, or ethyl cellulose, but bentonite is particularly preferred to use in terms of ease of handling. In addition to this, an example of preferred clay may include starch or silica.

Figure 1:
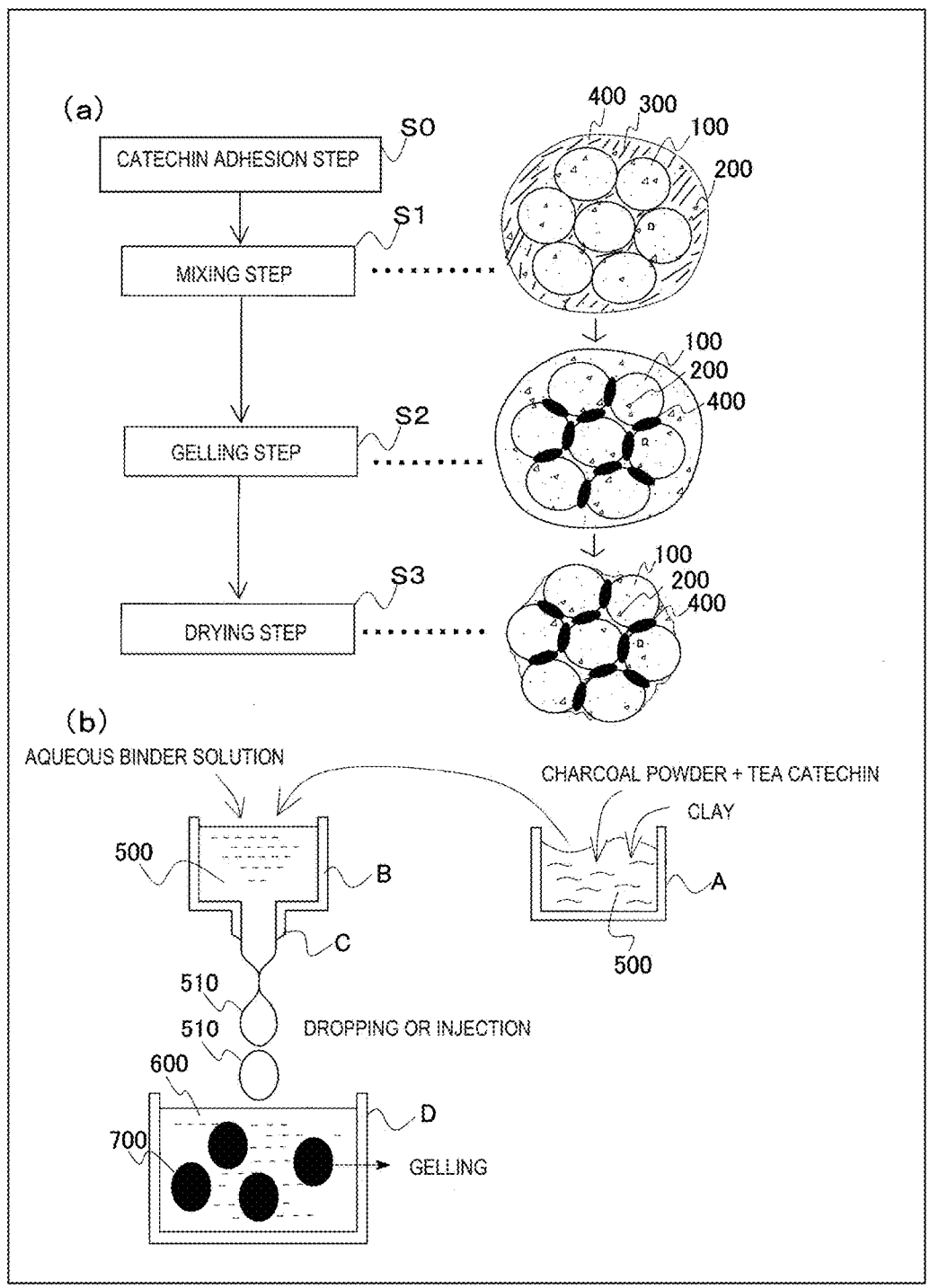
FIG. 1 illustrates a flowchart of a method for manufacturing a freshness retaining agent according to a first embodiment of the present invention and an explanatory diagram of a gel formation.

A method for manufacturing the freshness retaining agent according to the first embodiment will be described with reference to FIG. 1. FIG. 1 illustrates a flowchart of the method for manufacturing the freshness retaining agent according to the first embodiment of the present invention.

In the method for manufacturing the freshness retaining agent according to this embodiment, first, an aqueous binder solution consisting of a water-soluble polymer is mixed with tea catechins, charcoal powders, and clay, thereby obtaining a mixed solution.

As the water-soluble polymer, for example, any one of sodium alginate, potassium alginate, or ammonium alginate can be selected, but sodium alginate is preferably used in terms of ease of availability.

As illustrated in FIG. 1(a), first, an aqueous binder solution 3 (jelly shape) consisting of a water-soluble polymer is mixed with tea catechin 2, thereby producing jelly-like liquid catechin, and the jelly-like liquid catechin is mixed with charcoal powders 100, whereby the charcoal powder 100 and the tea catechin 200 adhere to each other in a state of being covered in the form of jelly (S0: catechin adhesion step). As also illustrated in FIG. 1(b), subsequent to step S0, a mixed solution 5 obtained by mixing with clay 4 is stored in a container A (S1: mixing step).

Subsequently, a gel-like body 7 (gel-shaped product) is obtained by dropping of the mixed solution 5 obtained in the mixing step S1 into a potassium or calcium-containing aqueous solution 6 (S2: gelling step). As the potassium or calcium-containing aqueous solution 6, for example, potassium chloride or calcium chloride can be used.

As illustrated in FIG. 1(b), the dropping can be performed in such a manner that the mixed solution 5 is transferred to a burette B and is then dropped or extruded into a container D storing the potassium or calcium-containing aqueous solution 6 from the tip of a nozzle C of the burette B. By this dropping, a surface treatment is performed on a droplet 510 of the mixed solution 500 containing the charcoal powder 100 and the tea catechin 200, and thus the gel-like body 700 (gel-shaped product) can be formed into particulates.

In order to facilitate dispersion of the gel-like body 700 (gel-shaped product), the dropping is preferably performed by stirring the potassium or calcium-containing aqueous solution 600 in the container D. The shape of the obtained gel-like body 700 has a correlation between concentration and viscosity of the aqueous solution concentration. That is, it is possible to control a desired gel shape using tendencies that shaping is facilitated when the viscosity of the aqueous solution is relatively low and the shape of the gel becomes small when the concentration of the aqueous solution is relatively high.

Subsequently, the gel-like body 7 obtained in the gelling step S2 is dried (S3: drying step). The drying in the drying step S3 may include natural drying at room temperature or sun drying, but is preferably performed by firing at 80° C. to 100° C. By this firing, a molecule of the tea catechin 200 can significantly adhere to the charcoal powder 100 without being decomposed. In contrast, when the firing temperature is lower than 80° C., the tea catechin 200 is easily eluted to the outside of the charcoal powder 100, and is difficult to adhere to the charcoal powder 100. Further, when the firing temperature is higher than 100° C., the molecule of the tea catechin 200 is thermally decomposed by itself with ease.

By this drying, the freshness retaining agent according to this embodiment is configured in which, as illustrated in FIG. 1(a), the charcoal powders 100 are firmly bonded to each other by the clay 400 and the jelly-like liquid phase formed by the aqueous binder solution 300 in the mixing step S1 is removed (an outer membrane of the liquid phase of the aqueous binder solution 300 is contracted and broken by the drying), so that the charcoal powder 1 is exposed to the outside (surface), a contact area of the charcoal powder 100 coming in contact with outside air increases, and higher gas adsorption performance can be achieved. As a result of the drying, the water-soluble polymer (for example, alginate) derived from the aqueous binder solution 300 may remain in the freshness retaining agent according to this embodiment. In this case, this freshness retaining agent can exhibit more excellent adsorption properties by an increase in viscosity or specific surface area (herein also referred to as porosity) caused by the water-soluble polymer.

The freshness retaining agent according to this embodiment obtained in this way is intended to achieve not only excellent adsorption performance but also humidity conditioning properties obtained by moisture-absorption properties (particularly, derived from the charcoal powder) that varies with time, antibacterial activity against bacteria such as *Staphylococcus aureus* or *Klebsiella pneumoniae*, and antifungal properties that suppress the growth of fungus (see Examples to be described below). In addition, from the viewpoint of effective utilization of resources or cost containment, there has a large advantage when the charcoal powder and the tea catechin as a raw material are obtained from woody biomass such as a neglected bamboo forest and a tea residual material.

In this way, as a combination of raw materials to be used to obtain the freshness retaining agent of the present invention, for example, the bamboo charcoal and the tea catechin are used as the charcoal powder 100, the bentonite is used as the clay 400, the sodium alginate is used as the water-soluble polymer constituting the aqueous binder solution 300, and the calcium chloride is used as the potassium or calcium-containing aqueous solution 600, but the raw materials are not limited thereto.

Furthermore, a silver compound preferably adheres to the surface and/or the inside of the charcoal powder. With respect to the adhesion of the silver compound, although the mixed solution is obtained by mixing of the tea catechin, the charcoal powder, and the clay with the aqueous binder solution consisting of the water-soluble polymer in the method for manufacturing the freshness retaining agent described above, silver ions ($Ag^+$) are formed in the mixed solution by additional mixing of the silver compound with the mixed solution, and other steps are the same as those of the manufacturing method described above. In the freshness retaining agent obtained in this way, the silver compound preferably adheres to the surface and/or the inside of the charcoal powder, and thus silver ions are blended, whereby the silver ions originated from the silver compound act on the target gas, adsorption performance of gas adsorption with respect to the target gas and antibacterial activity against bacteria can be simultaneously enhanced, and high freshness retaining performance is obtained.

Together with the raw materials described above, a dispersant may be used as a raw material of the freshness retaining agent according to this embodiment. When a dispersion state of the charcoal powder and the clay as the raw material is not good, the dispersant can be used as necessary to facilitate the dispersion state. As such a dispersant, for example, commercially available purified bentonite (for example, "BEN-GEL" produced by HOJUN Co., Ltd.) may be used, which mainly contains montmorillonite clay. The amount of purified bentonite is preferably 1 to 2 wt % with respect to the total weight of the charcoal powder and the clay.

In particular, when a cut flower is a target of the freshness retaining agent, polysaccharides can also be added to the freshness retaining agent to use for supply of an energy source of the cut flower. Further, purified vinegar liquor can also be added to the freshness retaining agent to use for the purpose of antibacterial effects or antiviral effects.

Second Embodiment

A freshness retaining agent according to a second embodiment can also be obtained by a change of the forming method of the gel-like body 700 in the gelling step S2 of the first embodiment.

In the above-described gelling step S2, the gel-like body 700 is formed using the aqueous binder solution consisting of the water-soluble polymer and the potassium or calcium-containing aqueous solution 600, but the gel-like body 700 (gel-shaped product) can also be obtained using a generally usable gelling agent in addition to the above method. Examples of such gelling agents include agar, agarose, gum arabic, pullulan, starch, gelatin, pectin, glucomannan, galactomannan, xanthane gum, dextrin, carrageenan, gellan gum, tamarind seed gum, ethyl cellulose, and propylene glycol. It is possible to obtain the above-described gel-like body 700 (gel-shaped product) using these gelling agents and to obtain a freshness retaining agent equal to that of the first embodiment.

Third Embodiment

As freshness retaining agent according to a third embodiment, a silver compound can adhere to the surface and/or the inside of the charcoal powder in the first or second embodiment. From the adhesion of the silver compound to the surface and/or the inside of charcoal powder, the silver compound acts on a gas, whereby adsorption performance of gas adsorption and antibacterial activity against bacteria are improved at the same time and higher freshness retaining performance is obtained. As a raw material of the silver compound, an aqueous solution of silver oxide or silver chloride can be used, but various silver ion-containing aqueous solutions which are commercially available can be additionally used.

Fourth Embodiment

A fourth embodiment provides a gas purification device configured using the freshness retaining agent according to any one of first to third embodiments.

A gas purification device 1 according to the fourth embodiment is configured to include a gas treatment unit 11 that performs an adsorption treatment of gas components contained in a target gas using the freshness retaining agent described above. The gas treatment unit 11 is configured using a storage container in which the plurality of freshness retaining agents are stored in a bundle. The gas components of the circulating target gas are adsorbed by action of the freshness retaining agent when the target gas simply passes through the storage container, and thus the target gas can be purified. In this embodiment, thus, it is possible to achieve purification of the target gas with a simple configuration.

Fifth Embodiment

As illustrated in FIG. 2(a), a gas purification device according to this embodiment is configured to include a titanium oxide treatment unit 12 having a coated surface coated with a titanium oxide, a light source unit 13 that irradiates the titanium oxide treatment unit with light, and a power source 14 that supplies power to the light source unit 13, in addition to the gas treatment unit 11 described in the fourth embodiment.

The titanium oxide treatment unit 12 preferably has a gas permeable vent hole. In addition, the titanium oxide treatment unit 12 can be made of a metal such as stainless or ceramic. As the light source unit 13, although various electric bulbs as a light source can be used, an LED is preferably used in terms of power saving performance, and an ultraviolet LED is particularly used in terms of intensity of irradiation energy. The power source 14 is not particularly limited as long as being a power source that supplies power to the light source unit 13. For example, a battery may be used with no change, but is more preferably incorporated with a control circuit that performs an ON/OFF control operation of the battery with time. When the control circuit is incorporated, it is possible to achieve power saving compared to a case where the battery becomes constantly an ON-state, maintain power for a long time, and perform a gas cleaning treatment for a long time.

A positional relation between the gas treatment unit 11, the titanium oxide treatment unit 12, and the light source unit 13 is not particularly limited; however, for example, as illustrated in FIG. 2(a), the light source unit 13 can be disposed oppositely to the coated surface of the titanium oxide treatment unit 12, and the titanium oxide treatment unit 12 can be disposed above the gas treatment unit 11. In this way, since the light source unit 13 is disposed oppositely to the coated surface of the titanium oxide treatment unit 12 and the titanium oxide treatment unit 12 is disposed above the gas treatment unit 11, the light source unit 13 irradiates the titanium oxide treatment unit 12 with light to exhibit photocatalytic action so that gas components contained the target gas passing through the titanium oxide treatment unit 12 are subjected to eradication of bacteria or degradation and sterilizing action, and the gas components contained in the target gas is subjected to an adsorption treatment by the action of the freshness retaining agent in the gas treatment unit 11, whereby the target gas is subjected to a cleaning treatment by multiple types of action and can be effectively maintained in a gas cleaning state for a long time.

Figure 2:
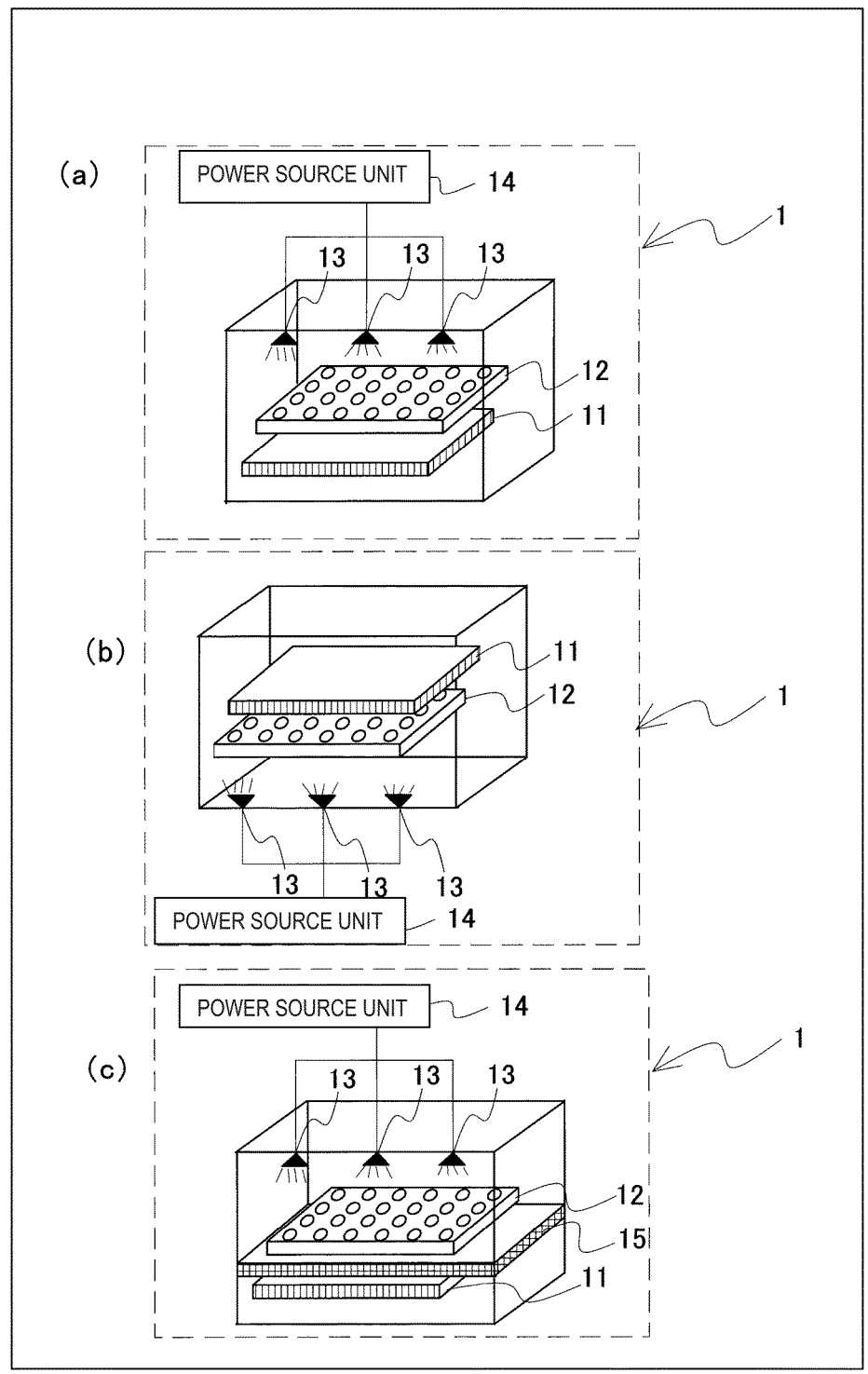
FIG. 2 illustrates an explanatory diagram of a structure of a gas purification device according to a fifth embodiment of the present invention.

In addition, the gas purification device according to this embodiment can also be configured such that, as illustrated in FIG. 2 (b), the light source unit 13 is disposed oppositely to the coated surface of the titanium oxide treatment unit 12 and the titanium oxide treatment unit 12 is disposed below the gas treatment unit 11. First, a target gas is subjected to eradication of bacteria, degradation, and a sterilizing treatment by passing through the titanium oxide treatment unit 12, and then gas components contained in the target gas is subjected to an adsorption treatment by action of the freshness retaining agent in the gas treatment unit 11, whereby the target gas is subjected to multiple cleaning treatments and can be effectively maintained in a gas cleaning state for a long time.

Furthermore, as illustrated in FIG. 2(c), the gas purification device according to this embodiment can also include a light shielding unit 15 that is disposed between the gas treatment unit 11 and the light source unit 13 to shield light. The light shielding unit 15 can be configured using a gallery formed into multi-layered pleats.

Since the light shielding unit 15 is disposed so that unnecessary light irradiation from the light source unit 13 is blocked with respect to the gas treatment unit 11, deterioration of the freshness retaining agent constituting the gas treatment unit 11 is prevented, an extra-service life of the freshness retaining agent is achieved, and thus gas cleaning performance can be maintained over a long period of time.

Sixth Embodiment

Figure 3:
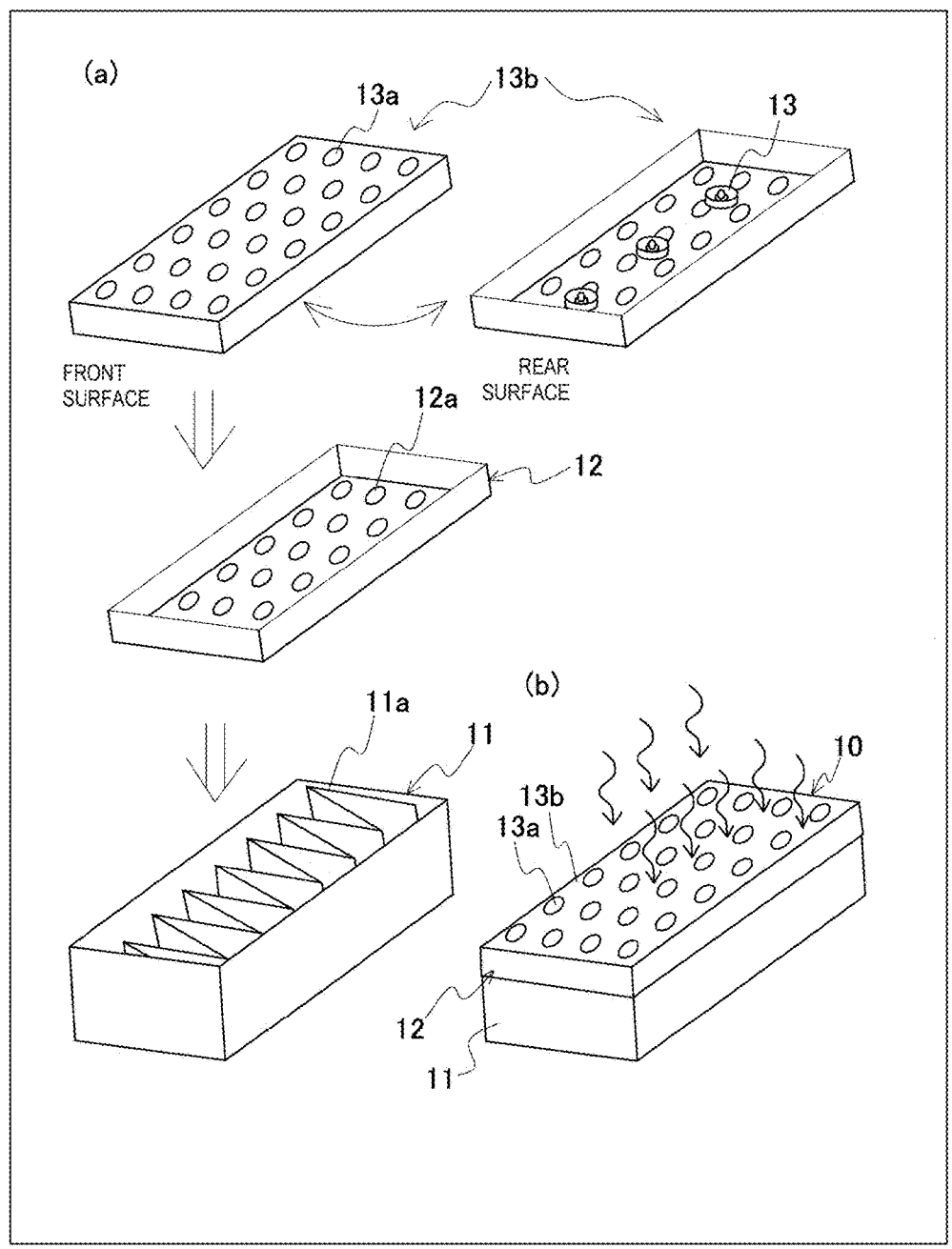
FIG. 3 illustrates an explanatory diagram of a structure of a gas purification device according to a sixth embodiment of the present invention.

As illustrated in FIG. 3, a sixth embodiment is configured as a compact box type of the gas purification device described in the fifth embodiment. As illustrated in FIG. 3(a), a gas purification device according to this embodiment is constituted by the gas treatment unit 11 that includes a storage container storing a plurality of bundle bodies 11a of the freshness retaining agent, the titanium oxide treatment unit 12 that has a plurality of vent holes 12a and has a coated surface coated with a titanium oxide on a top surface thereof, and an upper cover 13b that is fitted into a casing of the titanium oxide treatment unit 12, has the plurality of vent holes 13a, and is disposed with the light source unit 13 configured by the ultraviolet LED on a rear surface thereof.

The storage container constituting the gas treatment unit 11 includes passage holes for passing the gas on a bottom and/or a side.

With this configuration, the gas purification device according to this embodiment is formed as an integrated box body as illustrated in FIG. 3(b), so that when the target gas passes through the gas purification device, the gas components of the target gas can be cleaned in a multiple manners and the target gas can efficiently purified over a long period of time, by a combination of bactericidal performance due to the ultraviolet irradiated from the ultraviolet LED constituting the light source unit 13, antibacterial activity and degradation performance due to the titanium oxide activated as a photocatalyst, and adsorption performance due to action of the freshness retaining agent. In addition, since being formed as the integrated box body, the gas purification device is also easily carried and can be used as a compact handy-type gas purification device.

The gas purification device according to each of the above-described embodiments may be configured by only the gas treatment unit 11. In this case, since the power source 14 for supplying the power is also not necessary, the gas purification device can be configured with a lightweight and compact structure and more easily carried, thereby being capable of performing gas cleaning with ease even in a narrow space.

Seventh Embodiment

In a seventh embodiment, as illustrated in FIG. 4(a), the gas treatment unit 11, the titanium oxide treatment unit 12, the light source unit 13, the power source 14, and the light shielding unit 15 in the gas purification device described in the sixth embodiment are provided, and a fan 16 is further provided on a bottom to blow air by supply of the power from the power source 14. That is, the fan 16 is disposed on the bottom of the compact box-type gas purification device.

In the gas purification device according to this embodiment with this configuration, since the air is blown from the bottom by the fan 16, the target gas around the gas purification device is taken in the gas purification device with a stable air flow and is then subjected to the gas purification treatment, so that the gas components of the target gas is cleaned without staying and the target gas can stably and efficiently purified over a long period of time. Since being portable, even in a place where air flow of the target gas tends to stagnate, the gas purification device according to this embodiment can smoothly perform gas purification by air flow to be generated by the fan 16 as long as only being mounted on a desired location.

Eighth Embodiment

In an eighth embodiment, the titanium oxide treatment unit 12 in the gas purification device described in the seventh embodiment is configured not to be coated with the titanium oxide.

Figure 4:
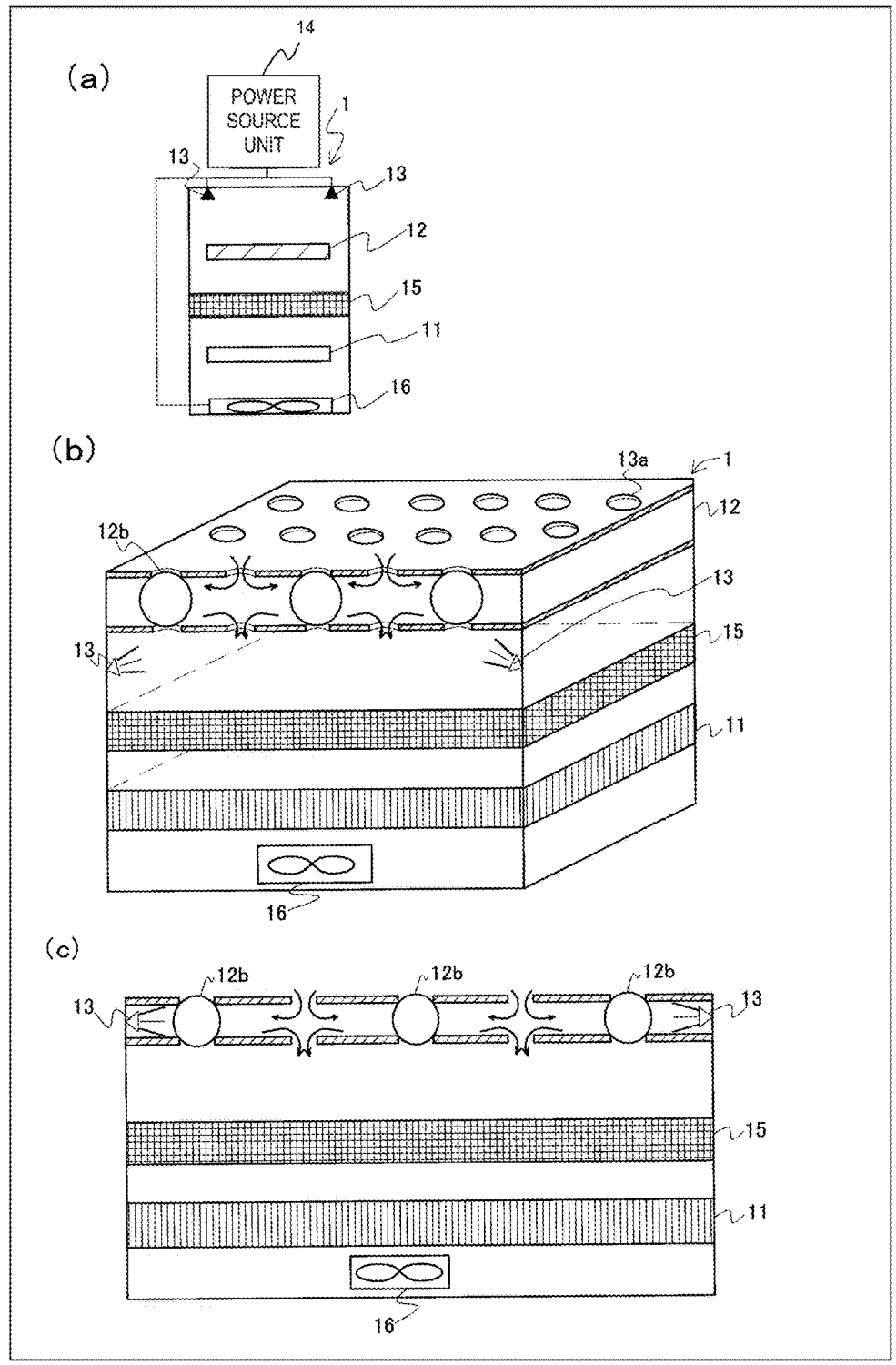
FIG. 4 illustrates an explanatory diagram (a) of a structure of a gas purification device according to a seventh embodiment of the present invention, and illustrates an explanatory diagram (b) and a cross-sectional view (c) of a structure of a gas purification device according to an eighth embodiment of the present invention.

In the gas purification device according to the eighth embodiment, as illustrated in FIG. 4 (b), the gas treatment unit 11, the titanium oxide treatment unit 12, the light source unit 13, the power source 14, and the light shielding unit 15 in the gas purification device described in the fifth or sixth embodiment are provided, and the titanium oxide treatment unit 12 includes spherical titanium oxide balls 12b that are fitted between the vent holes 12a and the vent holes 13a and are made of an titanium oxide. As illustrated in FIG. 4 (b), the light source unit 13 irradiates the titanium oxide balls 12b with light from the lower portion of the titanium oxide treatment unit 12.

The titanium oxide ball 12b is not particularly limited as long as being a spherical body containing the titanium oxide, but may be preferably constituted of a porous body. The titanium oxide ball 12b is constituted of the porous body, whereby the surface area is increased, the adsorption performance can be improved, the titanium oxide is easily carried, and the action of the photocatalyst can be enhanced. As such a porous body, for example, a silica gel may be used. The silica gel has high light permeability, whereby the irradiated light can be efficiently received, and the photocatalytic action can be enhanced by the titanium oxide to be carried. In the case of being constituted of the silica gel, the titanium oxide ball 12b is formed in such a manner that the spherical silica gel is impregnated with a titanium oxide solution and is then dried, and thus the titanium oxide is carried on from the surface to inside the silica gel.

In this way, not only the outer surface but also the inside of the spherical silica gel are significantly impregnated with the titanium oxide, whereby the titanium oxide ball 12b is irradiated with light from the light source unit 13 to exhibit photocatalytic action over a wide region of the outer surface and the inside thereof, a high sterilizing effect is realized with respect to the target gas, and a gas-cleaned state can be efficiently maintained for a long time.

Further, the titanium oxide ball 12b preferably makes use of a catalytic action-type titanium oxide even in a state of being hardly irradiated with light (even in a dark portion). In this case, since sufficient catalytic action is exerted even in a deep inside region of the silica gel that is hardly irradiated with light, the gas purification device according to this embodiment also realizes a high sterilizing effect with respect to the target gas and can efficiently maintain a gas-cleaned state for a long time.

In this way, the target gas passing through the titanium oxide treatment unit 12 three-dimensionally comes in contact with the spherical titanium oxide ball 12b having a three-dimensional shape, whereby a contact area of the target gas dramatically increases compared to a two-dimensional gas contact with the titanium oxide as in a case where a planar surface is coated, a degradation rate of the target gas is enhanced, and gas cleaning can be more efficiently performed.

The titanium oxide balls 12b are fixed by being fitted into some of vent holes 12a and vent holes 13a. The titanium oxide balls 12b are preferably disposed at equal intervals. From this configuration, the air flow is smoothly conducted in some of vent holes 12a and vent holes 13a into which the titanium oxide balls 12b are not fitted, and gas cleaning can be more efficiently performed by photocatalytic action due to the titanium oxide ball 12b without interruption of the air flow.

Since the titanium oxide ball 12b is fixed by the fitting and is freely detachable, the old and new exchange of the titanium oxide can be easily performed compared to a case of being coated with the titanium oxide, and time and cost related to maintenance of the device can be suppressed. In addition, since the number of the titanium oxide balls 12b can be freely changed depending on the degree (size or degree of contamination) of a gaseous environment of a space in which the gas purification device according to this embodiment is mounted, gas cleaning can be performed depending on the mounting space such that the number of the titanium oxide balls 12b is not excessive, and excellent cost-effectiveness can also be realized.

Furthermore, the titanium oxide ball 12b preferably includes a fine projection, which does not contain the titanium oxide, on the outer surface thereof. As such a projection, various kinds of ceramic or apatite is preferably used in terms of having its own adsorption performance.

When including the projection, the titanium oxide ball 12b is fitted into the vent hole 12a and the vent hole 13a through the projection, whereby the vent hole 12a and the vent hole 13a are fitted into the titanium oxide component in a non-contact state, and it is possible to prevent deterioration due to the photocatalytic action with respect to the titanium oxide treatment unit 12 and the upper cover 13b.

As illustrated in FIG. 4(c), the light source unit 13 can irradiate the titanium oxide ball 12b with light inside the titanium oxide treatment unit 12. In this case, since the light is irradiated near the titanium oxide ball 12b, the photocatalytic action can be more enhanced, and gas cleaning can be more efficiently performed.

The gas purification devices according to the first to eighth embodiments described above have a wide variety of application ranges and are not limited to the size of the target space of gas purification.

Moreover, from the viewpoint that the gas purification treatment can be efficiently performed, this gas purification device is preferably mounted a place in which air flow is forcibly generated by a fan installed at the outside, especially when the target space of gas purification is sufficiently large.

As an example, the above-described gas purification device 1 may be mounted inside a reefer container in which an air blowing unit 3 including the fan 3a is mounted. The reefer container is a container that is used to transport, for example, fresh food or medical goods having need of freezing or refrigeration and works of art or films that are deteriorated at a high temperature. When this gas purification device is mounted in the container, it is possible to achieve freshness maintenance over a long period of time, decomposition prevention, and deterioration prevention of these stored goods.

From this viewpoint, in the following embodiments, gas purification systems including the gas purification device 1 according to the first to eighth embodiments will be exemplified.

Ninth Embodiment

A gas purification system according to a ninth embodiment includes a droplet dissipating unit 2, which dissipates droplets to the target gas, in a front stage of the gas purification device 1.

Figure 5:
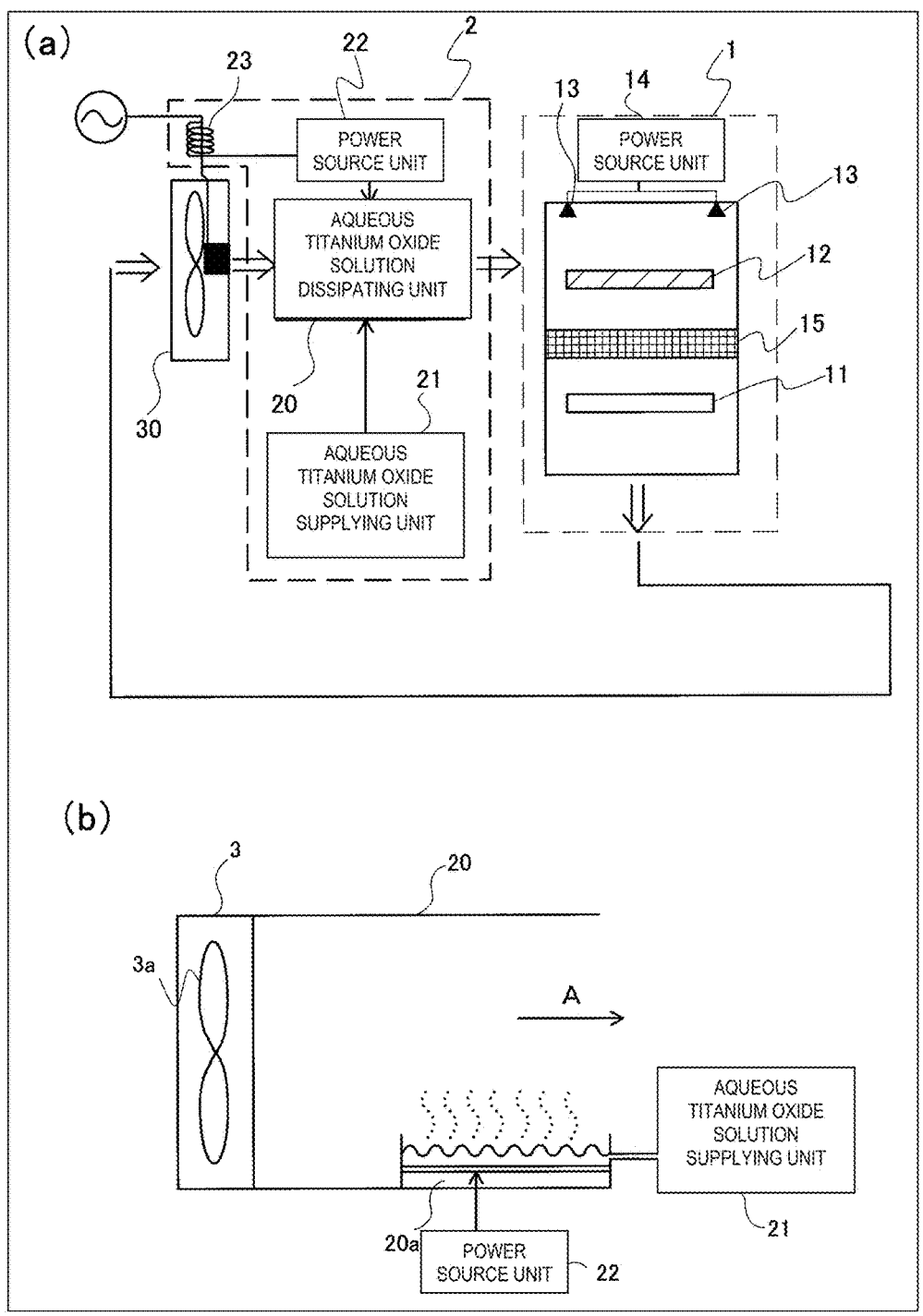
FIG. 5 illustrates a block diagram of a gas purification system according to a ninth embodiment of the present invention and an explanatory diagram of a structure of a titanium oxide dissipating unit.

As illustrated in FIGS. 5(a) and 5(b), the gas purification system according to the ninth embodiment includes: the gas purification device 1 including the gas treatment unit 11, the titanium oxide treatment unit 12, the light source unit 13, the power source 14, and the light shielding unit 15 as described in the fourth embodiment; and the droplet dissipating unit 2 including an aqueous titanium oxide solution supplying unit 21 that supplies an aqueous titanium oxide solution, an ultrasonic vibration unit 20a for generating ultrasonic vibration, which serves as an aqueous titanium oxide solution dissipating unit 20 dissipating droplets of the aqueous titanium oxide solution supplied by the aqueous titanium oxide solution supplying unit 21, and a power source 22 for supplying power to the ultrasonic vibration unit 20a, and the gas purification system has a configuration in which the target gas is supplied to the gas purification device 1 after passing through the aqueous titanium oxide solution dissipating unit 20.

The aqueous titanium oxide solution supplying unit 21 supplies the aqueous titanium oxide solution to the aqueous titanium oxide solution dissipating unit 20 and includes a container that stores the aqueous titanium oxide solution.

The aqueous titanium oxide solution dissipating unit 20 is not particularly limited as long as dissipating the droplets of the aqueous titanium oxide solution, but, in this embodiment, includes the ultrasonic vibration unit 20a for generating ultrasonic vibration and the power source 22 for supplying power to the ultrasonic vibration unit 20a as illustrated in FIG. 5(b). In terms of being efficiently contained in the target gas, the droplets of the aqueous titanium oxide solution have preferably a particle size from nanometer order to micrometer order, and more preferably have a particle size from 0.3 nm to 0.5 μm.

When the droplets of the aqueous titanium oxide solution have a particle size smaller than 0.3 nm, the droplets are hardly formed (the droplets hardly dissipate), and when having a particle size greater than 0.5 μm, the droplets hardly pass through various filters such as a nonwoven fabric in terms of size, dew condensation easily occurs, and thus fungi easily grow. Particularly, in the above-described gas purification device according to the eighth embodiment, the droplets have a particle size from 0.3 nm to 0.5 μm, and this is a size easy to enter voids of the porous body of the titanium oxide ball 12b. Therefore, when moving to the gas purification device 1, the floating droplets are efficiently taken in the titanium oxide ball 12b, whereby photocatalytic action is more enhanced in the titanium oxide ball 12b, a higher sterilizing effect is exerted with respect to the target gas, and a gas-cleaned state can be efficiently maintained for a long time.

As the ultrasonic vibration unit 20a, for example, a magnetic stirrer or a vibration stirrer may be used. With this configuration, droplets not obtained by simple air blowing-type or steam-type vaporization used in the related art, that is, droplets having a size containing at least an aqueous titanium oxide solution component are generated by ultrasonic vibration, and dissipate toward a direction A in FIG. 5(b). The droplets contain the aqueous titanium oxide solution component difficult to be contained by the simple vaporization of the related art, and thus are mixed with the target gas, whereby sterilizing activity originated from the titanium oxide is exerted with respect to the target gas, and a gas cleaning effect can be enhanced with respect to the target gas.

Further, the target gas mixed with the droplets containing the titanium oxide is supplied to the gas purification device 1, whereby the titanium oxide component contained in the droplets acts as a photocatalyst with light irradiation by the light source unit 13 to directly and additionally exhibit the sterilizing effect with respect to the target gas, sterilizing, bacterial killing, eradication of bacteria, and an adsorption treatment are performed in a multiple manner in the inside of the gas purification device 1, and highly efficient gas cleaning can be realized over a long period of time.

The power source 22 for supplying power to the aqueous titanium oxide solution dissipating unit 20 is not limited as long as being normal power, and may include, for example, a power acquisition unit 23 that extract power from a magnetic field generated in a current generated from the outside, as illustrated in FIG. 5(a). As the power acquisition unit 23, a coil may be used. With this configuration, even in a container having a condition that a receptacle cannot be disposed inside the gas purification system according to this embodiment, in particular, the power extracted by the power acquisition unit 23 is stably supplied to the aqueous titanium oxide solution dissipating unit 20, and gas cleaning can be continuously performed over a long period of time.

In addition, the power extracted by the power acquisition unit 23 can function as the power source 14 by being directly supplied to the light source unit 13. That is, one power source can be configured without the power source provided separately as the power source 14. In this case, for example, when the power extracted by the power acquisition unit 23 is changed with time, light irradiation of the light source unit 13 is also changed with time in conjunction with the change, dynamic gas cleaning can be performed in the gas purification device 1.

Tenth Embodiment

As illustrated in FIG. 6(a), similarly to the above-described gas purification system according to the eighth embodiment, a gas purification system according to a tenth embodiment includes: the gas purification device 1 including the gas treatment unit 11, the titanium oxide treatment unit 12, the light source unit 13, the power source 14, and the light shielding unit 15; and the droplet dissipating unit 2 including a decompression chamber 20b in which flash evaporation occurs, which serves as the aqueous titanium oxide solution dissipating unit 20, and the aqueous titanium oxide solution supplying unit 21.

The aqueous titanium oxide solution dissipating unit 20 generates and dissipates droplets having a size containing at least an aqueous titanium oxide solution component by the flash evaporation using the decompression chamber 20b. In this way, since the aqueous titanium oxide solution dissipating unit 20 generates droplets having a size containing at least an aqueous titanium oxide solution component by the flash evaporation using the decompression chamber 20b, and dissipates the droplets toward a direction A in FIG. 6(b), power for driving the aqueous titanium oxide solution dissipating unit 20 is not necessary, antibacterial action, sterilizing, degradation, and eradication of bacteria due to the titanium oxide are easily and reliably exerted with respect to the target gas even under a condition where the supply of power is difficult, and gas cleaning can be performed.

Other Embodiments

Figure 7:
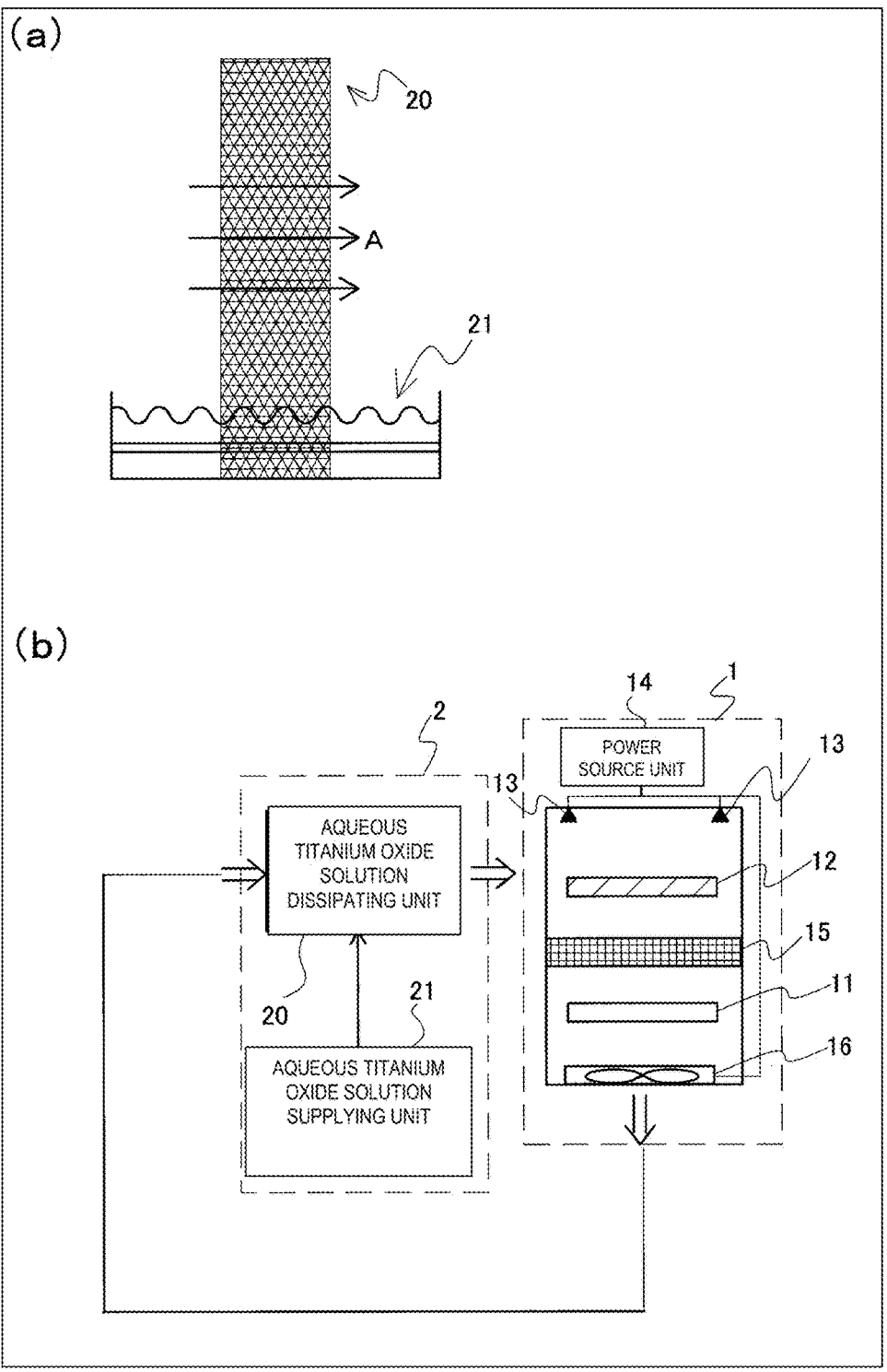
FIG. 7 illustrates an explanatory diagram and a block diagram of a structure of a titanium oxide dissipating unit of a gas purification system according to other embodiments of the present invention.

A gas purification system according to other embodiments can have a configuration in which as a modified example of the aqueous titanium oxide solution dissipating unit 20, as illustrated in FIG. 7 (a), the aqueous titanium oxide solution dissipating unit 20 generates and dissipates droplets having a size containing at least an aqueous titanium oxide solution component by a net body immersed in the aqueous titanium oxide solution of the aqueous titanium oxide solution supplying unit 21. With this configuration, the aqueous titanium oxide solution can be sucked up onto the net body by capillary action, the titanium oxide solution is contained in the target gas when the target gas passes through the net body, antibacterial action, sterilizing, degradation, and eradication of bacteria due to the titanium oxide are easily and reliably exerted with respect to the target gas with a simpler configuration even under a condition where the supply of power is difficult, and gas cleaning can be performed.

As illustrated in FIG. 7(b), similarly to the tenth embodiment, a gas purification system according to other embodiments includes: the gas purification device 1 including the gas treatment unit 11, the titanium oxide treatment unit 12, the light source unit 13, the power source 14, the light shielding unit 15, and the fan 16; and the droplet dissipating unit 2 including the aqueous titanium oxide solution dissipating unit 20, and the aqueous titanium oxide solution supplying unit 21, and thus the need for the air blowing unit 3 disposed outside the gas purification device 1 can be eliminated.

As described above, the aqueous titanium oxide solution dissipating unit 20 generates and dissipates droplets having a size containing at least an aqueous titanium oxide solution component by the net body immersed in the aqueous titanium oxide solution of the aqueous titanium oxide solution supplying unit 21. With this configuration, gas purification can be stably and continuously performed in the inside of the gas purification device 1 without depending on the presence or absence of air blowing and power from the outside.

Examples described herein are intended to exemplify the present invention, but not to limit the present invention.

Example 1

Bamboo charcoal, tea catechin, bentonite, sodium alginate, and calcium chloride were used as a raw material, and thus a freshness retaining agent was prepared. As a raw material of the tea catechin, tea leaves having a composition indicated in Table 1 below were used.

(Test Results of Dry Tea Leaves)

TABLE 1

| Variety | Type of Tea | | Caffeine | EGC | EGCg | EC | Ecg | (μg/ml) Total of Catechin |
|---|---|---|---|---|---|---|---|---|
| Saemidori | Kama | Open Field | 148.0 | 64.1 | 66.3 | 13.0 | 16.8 | 160.2 |

With respect to tea catechin extracts extracted from the tea leaves, five samples 1 to 5 having different concentrations of the tea leaves to water were obtained, and each catechin content was confirmed. The samples 1 to 5 were obtained by mixing water of 500 cc with respective tea leaves of 5 g, 10 g, 2.5 g, 5 g, and 7.5 g. In all of the samples, an extraction time was set to 15 minutes (boiling), and the samples 1 and 2 of these samples were subjected to extraction for 15 minutes and were additionally subjected to extraction for 15 minutes. The results are indicated in Table 2 below. From the obtained results, in the case of being subjected to extraction (boiling) for 15 minutes and being additionally subjected to extraction for 15 minute (samples 1 and 2), it was confirmed the stable amount of tea catechin was extracted.

TABLE 2

| No. | Concentration (tea leaves/water) | Variety | Tea 15 min. | Boiling + | Caffeine (mg/ml) | EGC (mg/ml) | EGCg (mg/ml) | EC (mg/ml) | Ecg (mg/ml) | Total of Catechin (mg/ml) |
|---|---|---|---|---|---|---|---|---|---|---|
| 1 | 5/500 | Saemidori | Extraction | 15 min. | 288 | 92.8 | 24.3 | 26.4 | 5 | 148.5 |
| 2 | 10/500 | Saemidori | Extraction | 15 min. | 506 | 183 | 42.4 | 49.9 | 7.7 | 283.1 |
| 3 | 2.5/500 | Saemidori | Extraction | — | 100.9 | 27.1 | 6.5 | 6.6 | 1.5 | 41.8 |
| 4 | 5/500 | Saemidori | Extraction | — | 138.5 | 54.9 | 20.8 | 11.7 | 3.6 | 91 |
| 5 | 7.5/500 | Saemidori | Extraction | — | 310.5 | 105 | 25.9 | 28.5 | 4.9 | 164.3 |

The bamboo charcoal was obtained by firing of commercially available bamboo at 600° C. to 800° C. With respect to other raw materials, commercially available bentonite (made by HOJUN Co., Ltd., Hotaka (main ingredient: $SiO_2$ of 68.6%, $Al_2O_3$ of 16.3%, $Fe_2O_3$ of 3.88%, CaO of 1.5%, and MgO of 1.72%)), sodium alginate (made by KIMICA Corporation), and calcium chloride (made by SHIRAIMATSU PHARMACEUTICAL CO., LTD.) were used.

(Manufacture of Freshness Retaining Agent)

Sodium alginate of 3 g was poured into water of 200 (ml) and was then dissolved with a mixer, thereby obtaining an aqueous solution of 300 g in total throughout a mixture of tea catechin. The sodium alginate aqueous solution was mixed with bamboo charcoal of 16 g and bentonite of 1.6 g, thereby obtaining a mixed solution A. Calcium chloride of 17 g was dissolved in water of 800 ml and was then left at the bottom of the container. The mixed solution A was dropped from a nozzle tip of a burette, thereby obtaining a gel-shaped product. At this time, the solution was dropped while being stirred using a stirrer such that the gel-shaped product was dispersed. The gel-shaped product was taken out of the container and then was dried after being cleaned with flowing cleaning-water. Thereafter, the gel-shaped product was dried at 100° C. in a furnace, thereby obtaining a freshness retaining agent.

Figure 8:
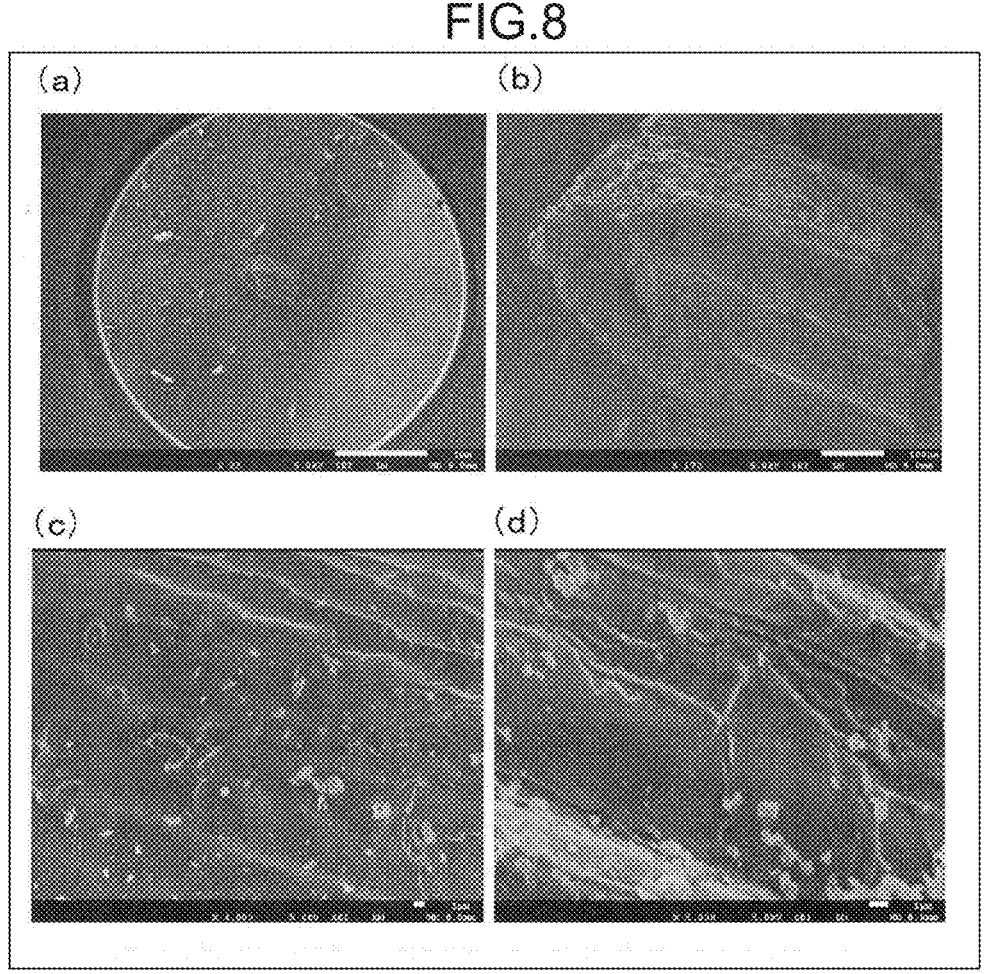
FIG. 8 illustrates a scanning electron microscope (SEM) image of the freshness retaining agent according to the embodiment of the present invention.

An scanning electron microscope (SEM) image of the obtained freshness retaining agent was obtained using an SEM apparatus (made by JEOL Ltd., JSM-7500F). The SEM image is illustrated in FIG. 8. In FIG. 8, the magnifying power of the SEM image is (a) 25 times, (b) 170 times, (c) 3000 times, and (d) 5000 times. From this result, it was found in the obtained freshness retaining agent that fine tea catechins were dispersed and adhered on/to the surface of the bamboo charcoal.

Figure 9:
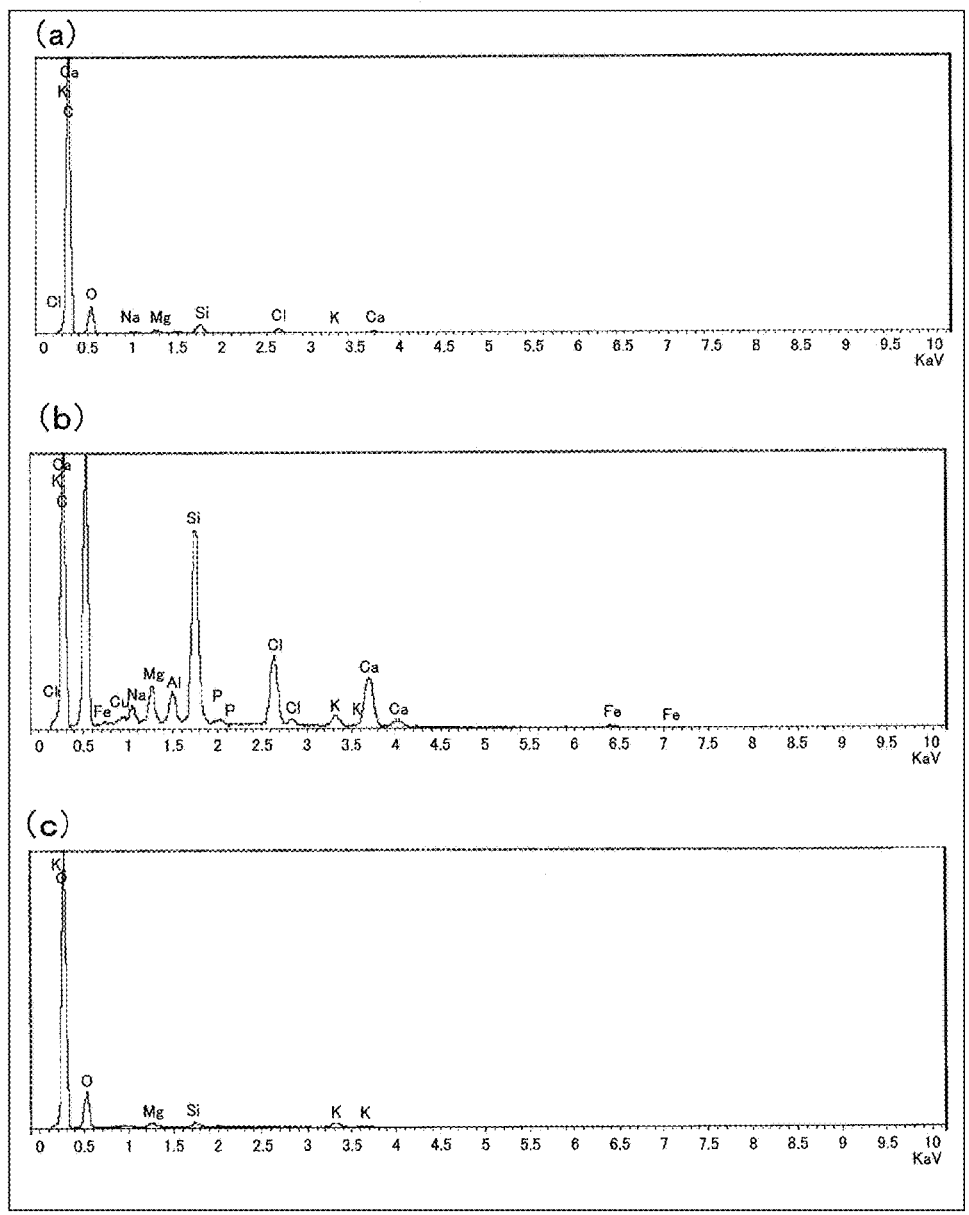
FIG. 9 illustrates a spectrum diagram obtained by energy dispersive X-ray spectroscopy (EDX) of the freshness retaining agent according to the embodiment of the present invention.

In addition, with respect to the obtained freshness retaining agent, elementary analysis was performed by energy dispersive X-ray spectroscopy (EDX) using an EDX apparatus (made by Oxford Instruments, Oxford INCA Energy type E2H). The results obtained from the elementary analysis are indicated in Tables 3 and 4, and corresponding spectrum diagrams are illustrated in FIGS. 9(a) and 9(b), respectively.

TABLE 3

| Element | Mass Concentration [%] | Number of Atoms Concentration [%] |
|---|---|---|
| C K | 77.36 | 82.74 |
| O K | 20.29 | 16.30 |
| Na K | 0.09 | 0.05 |
| Mg K | 0.21 | 0.11 |
| Si K | 0.85 | 0.39 |
| Cl K | 0.57 | 0.21 |
| K K | 0.10 | 0.03 |
| Ca K | 0.53 | 0.17 |
| Total | 100.00 | |

TABLE 4

| Element | Mass Concentration [%] | Number of Atoms Concentration [%] |
|---|---|---|
| C K | 45.00 | 56.22 |
| O K | 38.22 | 35.85 |
| Na K | 0.55 | 0.36 |
| Mg K | 1.12 | 0.69 |
| Al K | 0.84 | 0.47 |
| Si K | 6.06 | 3.24 |
| P K | 0.17 | 0.08 |
| Cl K | 3.30 | 1.40 |
| K K | 0.61 | 0.24 |

TABLE 4-continued

| Element | Mass Concentration [%] | Number of Atoms Concentration [%] |
|---|---|---|
| Ca K | 3.40 | 1.27 |
| Fe K | 0.34 | 0.09 |
| Cu L | 0.39 | 0.09 |
| Total | 100.00 | |

Furthermore, as a Comparative Example, with respect to only bamboo charcoal, elementary analysis was performed by energy dispersive X-ray spectroscopy, the results obtained from the elementary analysis are indicated in Table 5, and a corresponding spectrum diagram is illustrated in FIG. 9(c).

TABLE 5

| Element | Mass Concentration [%] | Number of Atoms Concentration [%] |
|---|---|---|
| C K | 72.96 | 78.80 |
| O K | 25.22 | 20.45 |
| Mg K | 0.45 | 0.24 |
| Si K | 0.49 | 0.23 |
| K K | 0.88 | 0.29 |
| Total | 100.00 | |

From these results, it was confirmed that the freshness retaining agent according to this Example in which the tea catechin was adhered to the bamboo charcoal had physical properties different from those of the bamboo charcoal.

Example 2

Adsorptive capacity for ammonia gas and acetaldehyde was confirmed using the freshness retaining agent obtained in Example 1 described above.

(Adsorption Test)

Testing Method: The freshness retaining agent (1 to 3) obtained in Example 1 described above and samples of comparative products (4 to 6) were put in a laboratory dish, and were put in a gas bag of 5 L. Air of 3 L was introduced to the gas bag, and ammonia gas was injected to be 30 ppm (even in a case of acetaldehyde, similarly, air of 3 L was introduced, and the acetaldehyde was injected to be 30 ppm). A concentration (initial n concentration) immediately after ammonia injection and a concentration after lapse of 15 minutes, 30 minutes, 45 minutes, 60 minutes, and 360 minutes were measured using a detection tube, and an adsorption rate D (%) was calculated using formula (I) below (similarly, a concentration (initial n concentration) immediately after acetaldehyde injection and a concentration after lapse of 15 minutes, 30 minutes, 45 minutes, 60 minutes, and 360 minutes were measured using a detection tube, and an adsorption rate D (%) was calculated using formula (I) below). The results are indicated in Table 1.

[Formula 1]

$$D(\%) = \frac{\text{Initial concentration (ppm)} - \text{Concentration after lapse of } n\text{-hour (ppm)}}{\text{Initial concentration (ppm)}} \times 100 \quad (I)$$

TABLE 6

| | Test Items | | Ammonia Adsorption Rate (%) (Initial Concentration 30 ppm) | | | | | Acetaldehyde Adsorption Rate (%) (Initial Concentration 30 ppm) | | | | |
|---|---|---|---|---|---|---|---|---|---|---|---|---|
| | | | 15 min. | 30 min. | 45 min. | 60 min. | 360 min. | 15 min. | 30 min. | 45 min. | 60 min. | 360 min. |
| Adsorption Test | Inventive Products | 1 | 87 | 99 | 100 | — | — | 46 | 93 | 100 | — | — |
| | | 2 | 88 | 100 | — | — | — | 86 | 95 | 100 | — | — |
| | | 3 | 97 | 100 | — | — | — | 43 | 93 | 95 | 100 | — |
| | Products of Other Companies | 4 | 16 | 20 | 33 | 40 | 51 | 20 | 41 | 45 | 51 | 89 |
| | | 5 | 13 | 18 | 32 | 38 | 48 | 21 | 39 | 43 | 48 | 90 |
| | | 6 | 20 | 23 | 38 | 41 | 47 | 20 | 42 | 47 | 49 | 88 |

Example 3

The adsorption performance with respect to the ammonia gas and the acetaldehyde was confirmed using the freshness retaining agent obtained in Example 1 together with the comparative example. As the comparative example, there have been considered the case of no adsorbent (blank) and the case of only the bamboo charcoal.

(Adsorption Test)

Ammonia was measured using twelve ammonia detector tubes 3 L (made by GASTEC) in the same procedure as that of Example (in the case of acetaldehyde, twenty-seven acetaldehyde detector tubes 3 L (made of GASTEC) were used). In the comparative example of only the bamboo charcoal, the bamboo charcoal of 15 g was used, and the freshness retaining agent of 15 g was used (in the case of acetaldehyde, the bamboo charcoal of 10 g was used in the comparative example of only the bamboo charcoal, and the freshness retaining agent of 9 g was used). The air of 3 L was introduced to the gas bag, and the ammonia gas was injected to be 15 ppm, and an absorption time was set to 45 seconds (even in a case of acetaldehyde, similarly, air of 3 L is introduced, the acetaldehyde is injected to be 30 ppm, and the absorption time was set to two minutes).

The results of the adsorption test for the ammonia gas and the acetaldehyde are respectively illustrated in FIGS. 10(a) and 10(b). In the case of ammonia, as can be seen from the results in the drawings, the ammonia concentration was almost eliminated after 15 minutes by the freshness retaining agent. On the contrary, in the case of only the bamboo charcoal of the comparative example, the ammonia of a concentration of 2.0 ppm was detected even after 15 minutes. Further, in the case of the adsorption test for the acetaldehyde, the acetaldehyde concentration was almost eliminated by the freshness retaining agent after 60 minutes elapses. On the contrary, in the case of only the bamboo charcoal of the comparative example, it took 90 minutes for eliminating the acetaldehyde concentration. Further, in the case of no adsorbent (blank), the ammonia gas and the acetaldehyde both remained in the initial concentration without decrease in concentration. In this way, the freshness retaining agent shows a remarkable adsorption performance not only in the case of no adsorbent but also in the case of only the bamboo charcoal with respect to the ammonia gas and the acetaldehyde.

Example 4

The freshness retaining effect was confirmed with respect to the flowers using the freshness retaining agent obtained in Example 1. As the flowers, commercially available carnations and tulips were employed.

(Freshness Retaining Agent Test)

Testing Method: Six commercially available carnations and tulips each were prepared and put into transparent vases (A and B: the freshness retaining agent obtained in Example 1, C and D: comparative products, and E and F: only the water). With these vases in this state, the test was performed two weeks on condition that an indoor temperature was set to 20 to 25 degrees and humidity was set to 50% to 70%. The results of changes in color of the flower, shrinkage, and fungus occurrence are listed in the following Table 1. In the freshness retaining agent (A and B) obtained in Example 1, there is no change in color, shrinkage, and fungus after 14 days. On the contrary, in the freshness retaining agent (C and D) of the comparative product, degradation in freshness was found particularly in color and shrinkage already after 3 days, and the degradation in freshness apparently appeared in day 7. Even in the case of only the water (E and F), the same tendency of degradation as shown in the freshness retaining agent (C and D) of the comparative product was found, but the freshness was particularly degraded to lose the commercial value after 10 days. As a result, it is found that the freshness retaining agent obtained in Example 1 can exhibit an excellent freshness retaining performance which has not found in the related art.

TABLE 7

| | | Day 0 | | | | Day 3 | | | | Day 7 | | |
|---|---|---|---|---|---|---|---|---|---|---|---|---|
| | | Color | Shrinkage | Fungus | Total | Color | Shrinkage | Fungus | Total | Color | Shrinkage | Fungus |
| A | | AA | AA | AA | AA | AA | AA | AA | AA | AA | AA | AA |
| B | | AA | AA | AA | AA | AA | AA | AA | AA | AA | AA | AA |
| C | | AA | AA | AA | AA | AA | BB | AA | AA | BB | BB | AA |
| D | | AA | AA | AA | AA | AA | AA | AA | AA | BB | AA | AA |
| E | | AA | AA | AA | AA | AA | BB | AA | AA | BB | BB | BB |
| F | | AA | AA | AA | AA | AA | BB | AA | AA | BB | BB | AA |

TABLE 7-continued

| | Day 7 | Day 10 | | | | Day 14 | | | |
|---|---|---|---|---|---|---|---|---|---|
| | Total | Color | Shrinkage | Fungus | Total | Color | Shrinkage | Fungus | Total |
| A | AA | AA | AA | AA | AA | AA | AA | AA | AA |
| B | AA | AA | AA | AA | AA | AA | AA | AA | AA |
| C | BB | BB | BB | AA | BB | CC | BB | AA | CC |
| D | AA | BB | BB | AA | BB | BB | BB | AA | BB |
| E | BB | CC | CC | BB | CC | — | — | — | — |
| F | BB | BB | CC | CC | CC | — | — | — | — |

AA: Not Changed
BB: Slightly Changed (Usable)
CC: Unusable
—: Stop

REFERENCE SIGNS LIST

1 Gas purification device
11 Gas treatment unit
12 Titanium oxide treatment unit
12a Vent hole
12b Titanium oxide ball
13 Light source unit
13a Vent hole
13b Upper cover
14 Battery
15 Light shielding unit
16 Fan
2 Droplet dissipating unit
20 Aqueous titanium oxide solution dissipating unit
20a Ultrasonic vibration unit
20b Decompression chamber
21 Aqueous titanium oxide solution supplying unit
22 Power source
23 Power acquisition unit
3 Air blowing unit
3a Fan
100 Charcoal powder
200 Tea catechin
300 Aqueous binder solution
400 Clay
500 Mixed solution
510 Droplet
600 Potassium or calcium-containing aqueous solution
700 Gel-like body
A Container
B Burette
C Nozzle
D Container

The invention claimed is:

1. A method for manufacturing a freshness retaining agent, comprising:
   a mixing step of mixing tea catechins, charcoal powders, and clay with each other to obtain a mixed solution;
   a gelling step of obtaining a gel-like body using a gelling agent with respect to the mixed solution obtained by the mixing step; and
   a drying step of drying the gel-like body obtained by the gelling step.

2. The method for manufacturing the freshness retaining agent according to claim 1,
   wherein the mixed solution is obtained in the mixing step by mixing the tea catechins, the charcoal powders, and the clay with an aqueous binder solution consisting of a water-soluble polymer, and
   the gel-like body is obtained in the gelling step by dropping the mixed solution obtained by the mixing step into a potassium or calcium-containing aqueous solution.

3. The method for manufacturing the freshness retaining agent according to claim 1,
   wherein the charcoal powder is one or more selected from bamboo charcoal, wood charcoal, or activated charcoal.

4. The method for manufacturing the freshness retaining agent according to claim 1,
   wherein the clay is one or more selected from bentonite, montmorillonite, hectorite, laponite, silica, starch, gelatin, guar gum, gum arabic, methyl cellulose, or ethyl cellulose.

5. The method for manufacturing the freshness retaining agent according to claim 1,
   wherein the water-soluble polymer is any one of sodium alginate, potassium alginate, or ammonium alginate, and
   the potassium or calcium-containing aqueous solution is either one of potassium chloride or calcium chloride.

6. The method for manufacturing the freshness retaining agent according claim 1,
   wherein the drying in the drying step is performed by firing at 80° C. to 100° C.

* * * * *